(12) United States Patent
Scates et al.

(10) Patent No.: US 8,686,201 B2
(45) Date of Patent: Apr. 1, 2014

(54) INTEGRATED ACID AND ALCOHOL PRODUCTION PROCESS HAVING FLASHING TO RECOVER ACID PRODUCTION CATALYST

(75) Inventors: Mark O. Scates, Houston, TX (US);
Ronald D. Shaver, Houston, TX (US);
James H. Zink, League City, TX (US);
Raymond J. Zinobile, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 132 days.

(21) Appl. No.: 13/292,818

(22) Filed: Nov. 9, 2011

(65) Prior Publication Data

US 2013/0116477 A1 May 9, 2013

(51) Int. Cl.
*C07C 27/04* (2006.01)

(52) U.S. Cl.
USPC ........................................................ 568/885

(58) Field of Classification Search
USPC ........................................................ 568/885
See application file for complete search history.

(56) References Cited

U.S. PATENT DOCUMENTS

| | | |
|---|---|---|
| 2,607,807 A | 8/1952 | Ford |
| 2,882,244 A | 4/1959 | Milton |
| 3,102,150 A | 8/1963 | Hunter et al. |
| 3,130,007 A | 4/1964 | Breck |
| 3,478,112 A | 11/1969 | Karl et al. |
| 3,709,795 A | 1/1973 | Singleton |
| 4,008,131 A | 2/1977 | Price |
| 4,039,395 A | 8/1977 | Eby |
| 4,107,002 A | 8/1978 | Eck et al. |
| 4,126,539 A | 11/1978 | Derr, Jr. et al. |
| 4,149,940 A | 4/1979 | Pinto |
| 4,317,918 A | 3/1982 | Takano et al. |
| 4,379,028 A | 4/1983 | Berg et al. |
| 4,395,576 A | 7/1983 | Kwantes et al. |
| 4,398,039 A | 8/1983 | Pesa et al. |
| 4,421,939 A | 12/1983 | Kiff et al. |
| 4,443,639 A | 4/1984 | Pesa et al. |
| 4,454,358 A | 6/1984 | Kummer et al. |
| 4,497,967 A | 2/1985 | Wan |
| 4,517,391 A | 5/1985 | Schuster et al. |
| 4,556,644 A | 12/1985 | Erpenbach et al. |
| 4,569,726 A | 2/1986 | Berg et al. |
| 4,629,711 A | 12/1986 | Erpenbach et al. |
| 4,664,753 A | 5/1987 | Erpenbach et al. |
| 4,678,543 A | 7/1987 | Houben et al. |
| 4,692,218 A | 9/1987 | Houben et al. |
| 4,737,318 A | 4/1988 | Ichino et al. |
| 4,777,303 A | 10/1988 | Kitson et al. |
| 4,804,791 A | 2/1989 | Kitson et al. |
| 4,985,572 A | 1/1991 | Kitson et al. |
| 4,990,655 A | 2/1991 | Kitson et al. |
| 4,992,582 A | 2/1991 | Ruppert et al. |
| 4,994,608 A | 2/1991 | Torrence et al. |
| 5,001,259 A | 3/1991 | Smith et al. |
| 5,026,908 A | 6/1991 | Smith et al. |
| 5,061,671 A | 10/1991 | Kitson et al. |
| 5,070,016 A | 12/1991 | Hallberg et al. |
| 5,144,068 A | 9/1992 | Smith et al. |
| 5,149,680 A | 9/1992 | Kitson et al. |
| 5,300,685 A | 4/1994 | Scates et al. |
| 5,399,752 A | 3/1995 | Okrasinski et al. |
| 5,414,161 A | 5/1995 | Uhm et al. |
| 5,416,237 A | 5/1995 | Aubigne et al. |
| RE35,377 E | 11/1996 | Steinberg et al. |
| 5,599,976 A | 2/1997 | Scates et al. |
| 5,696,284 A | 12/1997 | Baker et al. |
| 5,731,252 A | 3/1998 | Warner et al. |
| 5,821,111 A | 10/1998 | Grady et al. |
| 5,877,348 A | 3/1999 | Ditzel et al. |
| 5,883,295 A | 3/1999 | Sunley et al. |
| 5,932,764 A | 8/1999 | Morris et al. |
| 5,942,460 A | 8/1999 | Garland et al. |
| 5,993,610 A | 11/1999 | Berg |
| 6,140,535 A | 10/2000 | Williams |
| 6,143,930 A | 11/2000 | Singh et al. |

(Continued)

FOREIGN PATENT DOCUMENTS

| | | |
|---|---|---|
| CN | 1944373 | 4/2007 |
| CN | 1944374 | 4/2007 |

(Continued)

OTHER PUBLICATIONS

International Search Report and Written Opinion for PCT/US2011/060000 mailed Sep. 10, 2012.
Subramani et al., "A Review of Recent Literature to Search for an Efficient Catalytic Process for the Conversion of Syngas to Ethanol," Energy & Fuels, 2008, vol. 22, pp. 814-839.
Spivey et al., "Heterogeneous catalytic synthesis of ethanol from biomass-dervied syngas," Chemical Society Review, 2007, vol. 36, pp. 1514-1528.
Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

(Continued)

*Primary Examiner* — Johann R Richter
*Assistant Examiner* — Kofi Adzamli

(57) ABSTRACT

In one embodiment, the invention is to a process for producing ethanol, comprising the step of reacting carbon monoxide with at least one reactant in a reactor containing a reaction medium to produce a liquid reaction product comprising acetic acid. The process further comprises the step of separating the reaction product in a flasher into a liquid recycle stream and a vapor stream. The vapor stream is then distilled in a rectification tower and an overhead stream and an acetic acid stream are withdrawn therefrom, wherein the acetic acid is substantially free of halogen promoters. The process further comprises the step of hydrogenating acetic acid of the acetic acid stream in the presence of a second catalyst and under conditions effective to form a crude ethanol product comprising ethanol and water. Ethanol is recovered from the crude ethanol product.

20 Claims, 5 Drawing Sheets

(56) References Cited

U.S. PATENT DOCUMENTS

| | | |
|---|---|---|
| 6,232,352 B1 | 5/2001 | Vidalin et al. |
| 6,326,515 B1 | 12/2001 | Clode et al. |
| 6,375,807 B1 | 4/2002 | Nieuwoudt et al. |
| 6,458,996 B1 | 10/2002 | Muskett |
| 6,462,231 B1 | 10/2002 | Yanagawa et al. |
| 6,486,366 B1 | 11/2002 | Ostgard et al. |
| 6,495,730 B1 | 12/2002 | Konishi et al. |
| 6,509,180 B1 | 1/2003 | Verser et al. |
| 6,627,770 B1 | 9/2003 | Cheung et al. |
| 6,657,078 B2 | 12/2003 | Scates et al. |
| 6,685,754 B2 | 2/2004 | Kindig et al. |
| 6,906,228 B2 | 6/2005 | Fischer et al. |
| 6,927,048 B2 | 8/2005 | Verser et al. |
| 7,005,541 B2 | 2/2006 | Cheung et al. |
| 7,074,603 B2 | 7/2006 | Verser et al. |
| 7,084,312 B1 | 8/2006 | Huber et al. |
| 7,208,624 B2 | 4/2007 | Scates et al. |
| 7,351,559 B2 | 4/2008 | Verser et al. |
| 7,507,562 B2 | 3/2009 | Verser et al. |
| 7,553,397 B1 | 6/2009 | Colley et al. |
| 7,608,744 B1 | 10/2009 | Johnston et al. |
| 7,678,940 B2 | 3/2010 | Miura et al. |
| 7,682,812 B2 | 3/2010 | Verser et al. |
| 7,700,814 B2 | 4/2010 | Garton et al. |
| 7,834,223 B2 | 11/2010 | Atkins et al. |
| 7,842,844 B2 | 11/2010 | Atkins |
| 7,863,489 B2 | 1/2011 | Johnston et al. |
| 7,884,253 B2 | 2/2011 | Stites et al. |
| 7,906,680 B2 | 3/2011 | Scates et al. |
| 7,947,746 B2 | 5/2011 | Daniel et al. |
| 8,071,821 B2 | 12/2011 | Johnston et al. |
| 2003/0077771 A1 | 4/2003 | Verser et al. |
| 2006/0019360 A1 | 1/2006 | Verser et al. |
| 2007/0031954 A1 | 2/2007 | Mairal et al. |
| 2007/0270511 A1 | 11/2007 | Melnichuk et al. |
| 2008/0207953 A1 | 8/2008 | Houssin et al. |
| 2009/0023192 A1 | 1/2009 | Verser et al. |
| 2009/0069609 A1 | 3/2009 | Kharas et al. |
| 2009/0099389 A1 | 4/2009 | Shaver |
| 2009/0166172 A1 | 7/2009 | Casey et al. |
| 2009/0221725 A1 | 9/2009 | Chornet et al. |
| 2009/0299092 A1 | 12/2009 | Beavis et al. |
| 2009/0318573 A1 | 12/2009 | Stites et al. |
| 2009/0326080 A1 | 12/2009 | Chornet et al. |
| 2009/0326268 A1 | 12/2009 | Hanes et al. |
| 2010/0016454 A1 | 1/2010 | Gracey et al. |
| 2010/0029995 A1 | 2/2010 | Johnston et al. |
| 2010/0030001 A1 | 2/2010 | Chen et al. |
| 2010/0030002 A1 | 2/2010 | Johnston et al. |
| 2010/0041919 A1 | 2/2010 | Wu et al. |
| 2010/0063319 A1 | 3/2010 | Brtko et al. |
| 2010/0121114 A1 | 5/2010 | Johnston et al. |
| 2010/0137630 A1 | 6/2010 | Garton et al. |
| 2010/0145097 A1 | 6/2010 | Brtko et al. |
| 2010/0197485 A1 | 8/2010 | Johnston et al. |
| 2010/0197985 A1 | 8/2010 | Johnston et al. |
| 2010/0204512 A1 | 8/2010 | Kimmich et al. |
| 2011/0004033 A1 | 1/2011 | Johnston et al. |
| 2011/0046421 A1 | 2/2011 | Daniel et al. |
| 2011/0082322 A1 | 4/2011 | Jevtic et al. |
| 2011/0190547 A1 | 8/2011 | Jevtic et al. |
| 2011/0190548 A1 | 8/2011 | Jevtic et al. |
| 2011/0275861 A1 | 11/2011 | Johnston et al. |
| 2011/0275862 A1 | 11/2011 | Johnston et al. |
| 2012/0010439 A1 | 1/2012 | Jevtic et al. |
| 2012/0059197 A1 | 3/2012 | Jevtic et al. |
| 2012/0277483 A1 | 11/2012 | Horton et al. |
| 2013/0116476 A1 | 5/2013 | Lee et al. |
| 2013/0116478 A1 | 5/2013 | Johnston et al. |
| 2013/0116479 A1 | 5/2013 | Jevtic et al. |
| 2013/0116480 A1 | 5/2013 | Johnston et al. |

FOREIGN PATENT DOCUMENTS

| | | | |
|---|---|---|---|
| CN | 101665424 | 3/2010 | |
| CN | 102228831 | 11/2011 | |
| CN | 102229520 | 11/2011 | |
| DE | 241590 | 12/1986 | |
| EP | 0056488 | 7/1982 | |
| EP | 0104197 | 4/1984 | |
| EP | 0167300 | 1/1986 | |
| EP | 0175558 | 3/1986 | |
| EP | 0192587 | 8/1986 | |
| EP | 0198682 | 10/1986 | |
| EP | 0285420 | 10/1988 | |
| EP | 0285786 | 10/1988 | |
| EP | 0535825 | 4/1993 | |
| EP | 2060553 | 5/2009 | |
| EP | 2060555 | 5/2009 | |
| EP | 2072487 | 6/2009 | |
| EP | 2072488 | 6/2009 | |
| EP | 2072489 | 6/2009 | |
| EP | 2072492 | 6/2009 | |
| EP | 2186787 | 5/2010 | |
| JP | 6-116182 | 4/1994 | |
| JP | 2001-046874 | 2/2001 | |
| JP | 2005-289936 | 10/2005 | |
| WO | WO 83/03409 | 10/1983 | |
| WO | WO 02/092541 | 11/2002 | |
| WO | WO 2005/102513 | 11/2005 | |
| WO | WO 2007/003897 | 1/2007 | |
| WO | WO 2009/009320 | 1/2009 | |
| WO | WO 2009/063176 | 5/2009 | |
| WO | WO 2009-063176 A1 * | 5/2009 | ............ C07C 29/149 |
| WO | WO 2009063176 A1 * | 5/2009 | |
| WO | WO 2009/103948 | 8/2009 | |
| WO | WO 2009/105860 | 9/2009 | |
| WO | WO 2010/030320 | 3/2010 | |
| WO | WO 2010/055285 | 5/2010 | |

OTHER PUBLICATIONS

Acala, et al., (2005). Experimental and DFT studies of the conversion of ethanol and acetic acid on PtSn-based catalysts, Journal of Physical Chemistry, 109(6), 2074-2085.

Gauβ et al., "Synthesis of Acetic Acid and Acetic Acid Anydride from Methanol," Carbon Monoxide and Synthesis Gas Chemistry, pp. 104-138, (New York: VCH, 1996).

* cited by examiner

INTEGRATED ACID AND ALCOHOL PRODUCTION PROCESS HAVING FLASHING TO RECOVER ACID PRODUCTION CATALYST

FIELD OF THE INVENTION

The present invention relates generally to an integrated acid and alcohol production process and, in particular, to ethanol production processes that integrate acetic acid feed streams from a carbonylation process. The acetic acid feed streams may be obtained by reduced processing using a flashing step to recover the acid production catalyst, e.g., carbonylation catalyst.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are often formed with ethanol or are formed in side reactions. For example, during hydrogenation, esters are produced that together with ethanol and/or water form azeotropes, which are difficult to separate. These impurities may limit the production of ethanol and may require expensive and complex purification trains to separate the impurities from the ethanol. Also, the hydrogenation of acetic acid typically yields ethanol and water along with small amounts of side reaction-generated impurities and/or by-products. At maximum theoretical conversion and selectivity, the crude ethanol product would comprise approximately 72 wt. % ethanol and 28 wt. % water. In order to form purified ethanol, much of the co-produced water must be removed from the crude ethanol composition. In addition, when conversion is incomplete, unreacted acid may remain in the crude ethanol product. It is typically desirable to remove this residual acetic acid from the crude ethanol product to yield purified ethanol.

Some processes for integrating acetic acid production and hydrogenation have been proposed in literature. Generally, acetic acid production produces glacial acetic acid that has less than 1500 wppm water.

Previous literature discusses various integrated processes. For example, U.S. Pat. No. 7,884,253 discloses methods and apparatuses for selectively producing ethanol from syngas. The syngas is derived from cellulosic biomass (or other sources) and can be catalytically converted into methanol, which in turn can be catalytically converted into acetic acid or acetates. The ethanoic acid product may be removed from the reactor by withdrawing liquid reaction composition and separating the ethanoic acid product by one or more flash and/or fractional distillation stages from the other components of the liquid reaction composition such as iridium catalyst, ruthenium and/or osmium and/or indium promoter, methyl iodide, water and unconsumed reactants which may be recycled to the reactor to maintain their concentrations in the liquid reaction composition.

EP2060553 discloses a process for the conversion of a carbonaceous feedstock to ethanol wherein the carbonaceous feedstock is first converted to ethanoic acid, which is then hydrogenated and converted into ethanol.

U.S. Pat. No. 4,497,967 discloses an integrated process for the preparation of ethanol from methanol, carbon monoxide and hydrogen feedstock. The process esterifies an acetic anhydride intermediate to form ethyl acetate and/or ethanol.

U.S. Pat. No. 7,351,559 discloses a process for producing ethanol including a combination of biochemical and synthetic conversions results in high yield ethanol production with concurrent production of high value co-products. An acetic acid intermediate is produced from carbohydrates, such as corn, using enzymatic milling and fermentation steps, followed by conversion of the acetic acid into ethanol using esterification and hydrogenation reactions.

In carbonylating methanol, there have been proposals to reduce the purification train. US Pub. No. 2010/0145097 describes flashing and distilling the acetic acid reaction mixture in a flash tank equipped with a distillation column. WO Pub. No. 2010/030320 describes a process for producing acetic acid in which the use of a flash tank is eliminated. CN 200910089323.1 describes an acetic acid production that combines functions of conventional light end removal tower and dewatering tower and carries out the same in one rectification tower.

As such, the need remains for improvements in the integration of acetic acid production and ethanol production.

SUMMARY OF THE INVENTION

In a first embodiment, the present invention is directed to a process for producing ethanol. The process comprises the step of reacting carbon monoxide with at least one reactant in a reactor containing a reaction medium to product a reaction product comprising acetic acid. The reaction medium comprises water, acetic acid, methyl acetate, a halogen promoter and a first catalyst. The process further comprises the step of separating the reaction product in a flasher into a liquid recycle stream and a vapor stream. The vapor stream comprises acetic acid, the halogen promoter, methyl acetate and water. The process further comprises the step of distilling the vapor stream in a rectification tower and withdrawing an overhead stream and an acetic acid feed stream at a point below where the vapor stream is introduced to the tower. The overhead stream comprises substantially all of the water from the reaction product. The process further comprises the step of hydrogenating acetic acid of the acetic acid feed stream in the presence of a second catalyst and under conditions effective to form a crude ethanol product. The process further comprises the step of recovering ethanol from the crude ethanol product.

In a second embodiment, the present invention is directed to a process for producing ethanol. The process comprises the step of reacting carbon monoxide with at least one reactant in a reactor containing a reaction medium to produce a reaction product comprising acetic acid. The reaction medium comprises water, acetic acid, methyl acetate, a halogen promoter, and a first catalyst. The process further comprises the step of separating the reaction product in a flasher into a liquid recycle stream and a vapor stream comprising acetic acid, the halogen promoter, methyl acetate and water. The process further comprises the step of adding a washing liquid to the flasher to remove catalyst from a vapor phase such that the vapor stream comprises substantially no catalyst. The process further comprises the step of distilling the vapor stream in a rectification tower and withdrawing an acetic acid feed stream at a point below where the vapor stream is introduced to the tower. The process further comprises the step of hydrogenating acetic acid of the acetic acid feed stream in the presence of a second catalyst and under conditions effective to form a crude ethanol product. The process further comprises the step of separating at least a portion of the crude ethanol product to yield a distillate and a residue. The distillate comprises ethanol, water and ethyl acetate, and the residue comprises acetic acid and water. The washing liquid comprises a portion of the residue.

In a third embodiment, the present invention is directed to a process for producing ethanol. The process comprises the step of reacting carbon monoxide with at least one reactant in a reactor containing a reaction product comprising acetic acid. The reaction medium comprises water, acetic acid, methyl acetate, a halogen promoter, and a first catalyst. The process further comprises the step of separating the reaction product in a flasher into a liquid recycle stream and a vapor stream. The vapor stream comprises acetic acid, the halogen promoter, methyl acetate and water. The process further comprises the step of adding a washing liquid to the flasher to remove catalyst from a vapor phase such that the vapor stream comprises substantially no catalyst. The process further comprises the step of distilling the vapor stream in a rectification tower to form acetic acid feed stream and an overhead stream. The washing liquid comprises a portion of the overhead stream. The process further comprises the step of hydrogenating acetic acid of the acetic acid feed stream in the presence of a second catalyst and under conditions effective to form a crude ethanol product. The process further comprises the step of recovering ethanol from the crude ethanol product.

BRIEF DESCRIPTION OF DRAWINGS

The invention is described in detail below with reference to the appended drawings, wherein like numerals designate similar parts.

DETAILED DESCRIPTION OF THE INVENTION

Figure 1:
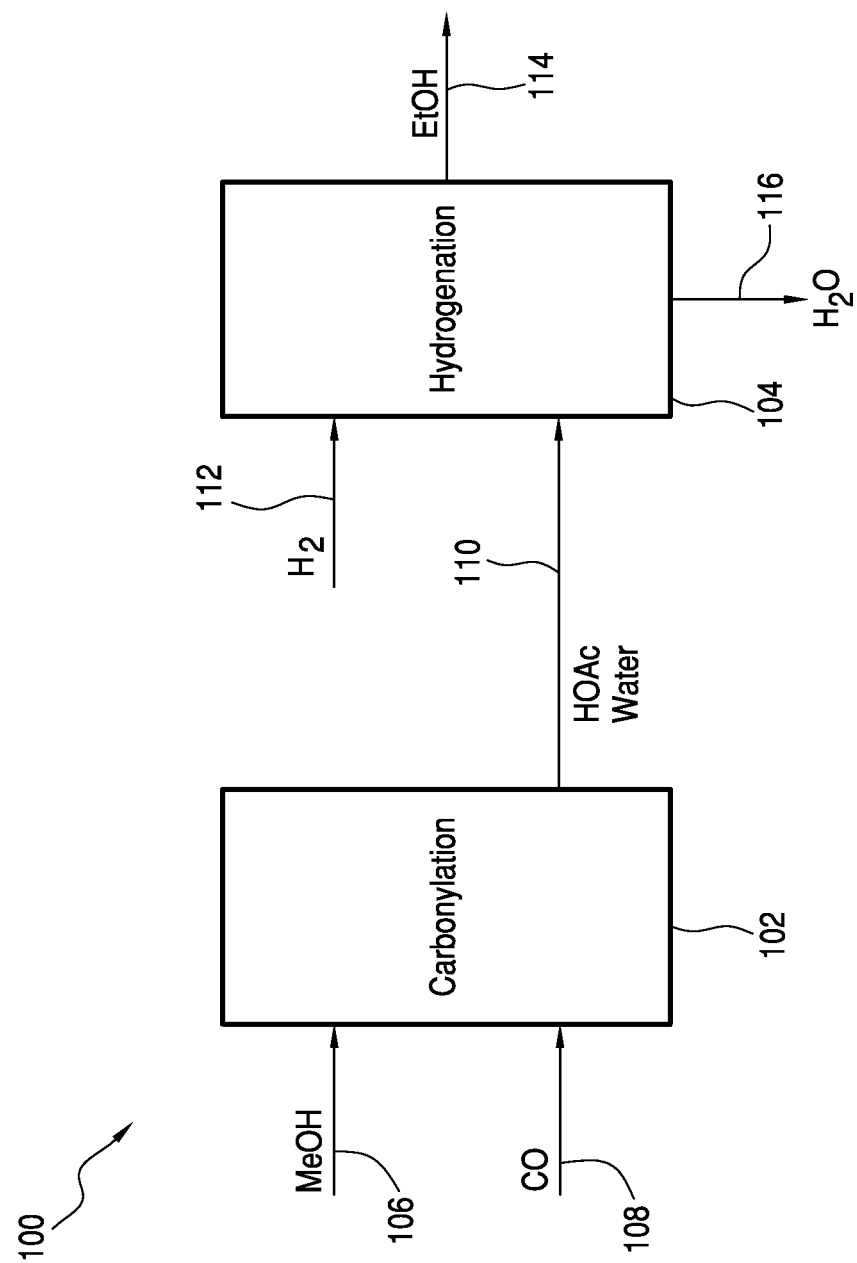
FIG. 1 is a diagram of an acetic acid and ethanol integrated production process in accordance with one embodiment of the present invention.

The present invention relates to integrated processes for producing acetic acid and ethanol. By reducing the purification of acetic acid, the overall efficiency in producing ethanol may be improved. In one embodiment, the purification of acetic acid uses one column, preferably one rectification tower for removing impurities. An acetic acid stream, which is suitable for hydrogenating to ethanol, may be obtained from the rectification tower. The impurities that are removed include methyl iodide, permanganate reducing compounds ("PRC's"), methanol, methyl acetate, methyl formate, and/or dimethyl ether. In general, these components may cause additional alcohols to be formed in the ethanol production process that would lead to further separation costs to recovery ethanol. In addition, the presence of methanol, methyl acetate, methyl formate, and/or dimethyl in the ethanol production process may lead to the production of off-spec ethanol. However, some of these impurities, such as PRC's, may also be hydrogenated to ethanol. Thus, the present invention reduces the separation steps necessary to produce an acetic acid feed for the ethanol production system.

In one embodiment, the acetic acid is purified using one column. Additional columns may be used for processing derivative streams, such a PRC's removal system. In general, the catalyst from is removed in a flash vessel and the volatile vapor phase is fed to one column. For purposes of the present invention the one column may be referred to as a combined light ends/dehydrating column. Reducing the number of columns reduces capital requirements. This may allow for small-scale integration processes that may be mobile. A mobile integrated process may be useful in converting remote carbon sources, such as stranded gas in the ocean, to ethanol.

The acetic acid stream obtained from the carbonylation process may be fed through a hydrogenation reaction to produce a crude ethanol product comprising ethanol and water, generally in equal molar ratios. Due to the reduced purification, there may be more water in the acetic acid than would otherwise be present in industrial grade acetic acid. Including water in the acetic acid feed stream would be expected to be detrimental to ethanol production because water is a co-product of the reaction and is not converted during hydrogenation. However, it has been found that feeding acetic acid and water in combination to a hydrogenation reactor does not substantially affect the conversion of acetic acid to ethanol and advantageously increases the efficiency of recovering ethanol from the resulting crude ethanol product.

The acetic acid stream from the rectification column may be fed through a hydrogenation reaction to produce a crude ethanol product comprising ethanol and water, generally in equal molar ratios. In one embodiment, a water stream may be separated from the crude ethanol product and returned to the flasher, where the water stream may be used to remove the catalyst and halogen promoter in the residue of the flasher. Furthermore, by removing water prior to the hydrogenation reaction may allow for more efficient ethanol separation that requires less energy.

In one embodiment, the rectification tower removes water in an amount more than 90%, e.g., more than 95%, more than 97% or more than 99%. In terms of ranges the rectification tower removes from 50% to 99% of water, e.g., from 65% to 99% of water, from 85% to 97% of water, or from 90% to 95% of water. In one embodiment, the rectification tower removes more than 90% halogen promoter from the reaction product in the overhead stream, e.g., removes more than 95%, more than 97%, more than 98%, or more than 99%. In terms of ranges, the rectification tower removes from 50% to 99% of the halogen promoter from the reaction product in the overhead stream, e.g., removes from 70% to 99%, from 85% to 98%, or from 90% to 95%. In one embodiment, the rectification tower removes more than 90% of methyl acetate from the reaction product in the overhead stream, e.g., removes more than 95%, more than 97%, more than 98%, or more than 99%. In terms of ranges, the rectification tower removes from 50% to 99% of methyl acetate from the reaction product in the overhead stream, e.g., removes from 70% to 99%, from 85% to 98%, or from 90% to 95%.

In one embodiment, the acetic acid feed stream comprises less than 10% of the water from the reaction product, e.g., less than 5% of water, less than 3%, or less than 1%. In terms of ranges, the acetic acid feed stream comprises from 50% to 1% of water from the reaction product, e.g., from 35% to 1% of water, from 15% to 3% of water, or from 10% to 5% of water. In one embodiment the acetic acid feed stream comprises less than 10% of halogen promoter from the reaction product, e.g., less than 5%, less than 3%, or less than 1%. In one embodiment, the acetic acid feed stream is of the halogen promoter, e.g., less than 1%, less than 2% or less than 3%. In one embodiment, the acetic acid feed stream comprises less than 10% of methyl acetate from the reaction product, e.g., less than 5%, less than 3%, or less than 1%.

In one embodiment, the vapor stream from the flasher is substantially free of a first catalyst, e.g., less than 5%, less than 3% or less than 1%. In one embodiment, the overhead stream of the rectification tower substantially free of a first catalyst, e.g., less than 5%, less than 3% or less than 1%. In one embodiment, the acetic acid feed stream substantially free of a first catalyst, e.g., less than 5%, less than 3% or less than 1%.

In one embodiment, the acetic acid feed stream comprises water in amounts of up to 25 wt. %, e.g., up to 20 wt. % water, or up to 10 wt. % water. In terms of ranges the acetic acid feed stream may comprise from 0.15 wt. % to 25 wt. % water, e.g., from 0.2 wt. % to 20 wt. %, from 0.5 to 15 wt. %, or from 4 wt. % to 10. wt. %. In one embodiment, the acetic acid feed stream that is provided to the ethanol production process comprises water in an amount of at least 1500 wppm, e.g., at least 2500 wppm, at least 5000 wppm, or at least 1 wt. %. The remaining portion of the feed stream to the ethanol process preferably comprises acetic acid and hydrogen, preferably in a molar ratio of hydrogen to acetic acid from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1. In some embodiments, the acetic acid feed stream may also comprise other carboxylic acids and anhydrides, as well as optionally acetaldehyde and/or acetone. In particular, the acetic acid feed stream may comprise methyl acetate and/or propanoic acid. These other compounds may also be hydrogenated in the processes of the present invention.

Surprisingly and unexpectedly, the presence of water in amounts of up to 25 wt. % does not significantly reduce acetic acid conversion or selectivity to ethanol. For purposes of the present invention, the term "conversion" refers to the amount of acetic acid in the feed that is converted to a compound other than acetic acid. Conversion is expressed as a mole percentage based on acetic acid in the feed. Selectivity is expressed as a mole percent based on converted acetic acid. It should be understood that each compound converted from acetic acid has an independent selectivity and that selectivity is independent of conversion. Although conversion and selectivity to ethanol may vary depending on the reaction conditions and catalyst, the presence of water does not result in significant variations to the acetic acid conversion or selectivity to ethanol.

In one embodiment, the acetic acid may be produced from a carbonylation process. Conventional carbonylation processes yield a glacial acetic acid product comprising less than 1500 wppm water, e.g., less than 500 wppm, or less than 100 wppm. This product typically requires an energy intensive dehydrating step to achieve these low water levels. Due to the reduced purification train, by using one distillation column, the embodiments of the present invention may produce an acetic acid product that contains more water.

FIG. 1 is a diagram of an integrated process 100 in accordance with the present invention. Process 100 comprises carbonylation zone 102 and hydrogenation zone 104. Carbonylation zone 102 receives methanol feed 106 and carbon monoxide feed 108. The methanol and the carbon monoxide are reacted in carbonylation zone 102 to form a crude product comprising acetic acid and water. A flasher may be used to remove residual catalyst from the crude product. For purposes of the present invention, carbonylation zone 102 comprises a purification train that contains only one distillation column to separate crude product into an acetic acid product stream 110 comprising from 0.15 wt. % to 25 wt. % water.

Acetic acid product stream 110 is fed, more preferably directly fed, to hydrogenation zone 104. Water is already present in acetic acid product stream 110 and generally it is not necessary to further add water, e.g., to co-feed water. Thus, the water fed to hydrogenation zone 104 is preferably provided by acetic acid product stream 110. Hydrogenation zone 104 also receives hydrogen feed 112. In hydrogenation zone 104, the acetic acid in acetic acid product stream is hydrogenated to form a crude ethanol product comprising ethanol and other compounds such as water, ethyl acetate, and unreacted acetic acid. Hydrogenation zone 104 further comprises one or more separation units, e.g. distillation columns, for recovering ethanol from the crude ethanol product. An ethanol product stream 114 may be recovered from hydrogenation zone 104. In addition, a water stream 116 may be separated and returned to the carbonylation zone 102 as a wash stream.

The process of the present invention may be used with any hydrogenation process for producing ethanol. The materials, catalysts, reaction conditions, and separation processes that may be used in the carbonylation of methanol and hydrogenation of acetic acid are described further below.

The raw materials, methanol, carbon monoxide, and hydrogen, used in connection with the process of this invention may be derived from any suitable source including natural gas, petroleum, coal, biomass, and so forth.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid and ethanol from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described integrated process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolyzed with additional natural gas to form syngas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into syngas, and U.S. Pat. No. 6,685,754, which discloses a method for the production of a hydrogen-containing gas composition, such as syngas including hydrogen and carbon monoxide, are incorporated herein by reference in their entireties.

Figure 2:
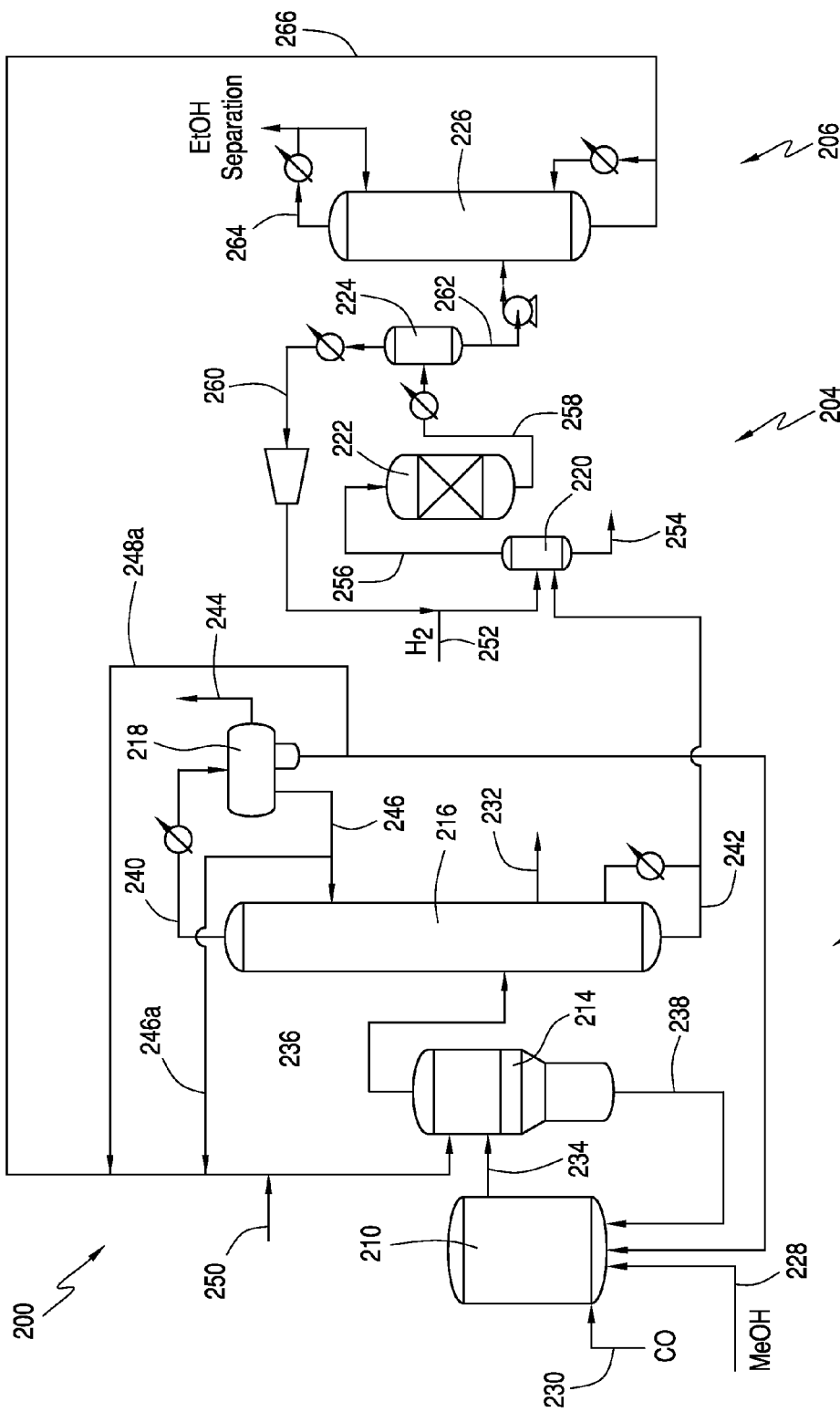
FIG. 2 is a schematic diagram of an exemplary integrated carbonylation and hydrogenation process in accordance with one embodiment of the present invention.

As shown in FIG. 2, and described further herein, carbonylation zone 202 preferably comprises a reactor 210, a flasher 214, and one rectification tower 216. Carbonylation zone 202 preferably comprises no other columns for further processing acetic acid, and the acetic acid obtained from rectification tower 216 is preferably directly fed to hydrogenation reaction zone 204. In one embodiment, carbon monoxide is reacted with methanol in a suitable reactor 210, e.g., a continuous stirred tank reactor ("CSTR") or a bubble column reactor. Preferably, the carbonylation process is a low water, catalyzed, e.g., rhodium-catalyzed, carbonylation of methanol to acetic acid, as exemplified in U.S. Pat. No. 5,001,259, which is hereby incorporated by reference.

Carbonylation Reaction

The carbonylation reaction may be conducted in a homogeneous catalytic reaction system comprising a reaction solvent, methanol and/or reactive derivatives thereof, a Group VIII catalyst, at least a finite concentration of water, and optionally an iodide salt.

Suitable catalysts include Group VIII catalysts, e.g., rhodium and/or iridium catalysts. When a rhodium catalyst is utilized, the rhodium catalyst may be added in any suitable form such that the active rhodium catalyst is a carbonyl iodide complex. Exemplary rhodium catalysts are described in Michael Gauβ, et al., *Applied Homogeneous Catalysis with Organometallic Compounds: A Comprehensive Handbook in Two Volume*, Chapter 2.1, p. 27-200, (1$^{st}$ ed., 1996). Iodide salts optionally maintained in the reaction mixtures of the processes described herein may be in the form of a soluble salt of an alkali metal or alkaline earth metal or a quaternary ammonium or phosphonium salt. In certain embodiments, a catalyst co-promoter comprising lithium iodide, lithium acetate, or mixtures thereof may be employed. The salt co-promoter may be added as a non-iodide salt that will generate an iodide salt. The iodide catalyst stabilizer may be introduced directly into the reaction system. Alternatively, the iodide salt may be generated in-situ since under the operating conditions of the reaction system, a wide range of non-iodide salt precursors will react with methyl iodide or hydroiodic acid in the reaction medium to generate the corresponding co-promoter iodide salt stabilizer. For additional detail regarding rhodium catalysis and iodide salt generation, see U.S. Pat. Nos. 5,001,259; 5,026,908; and 5,144,068, which are hereby incorporated by reference.

When an iridium catalyst is utilized, the iridium catalyst may comprise any iridium-containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include: $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H^+$, $[Ir(CO)_2I_4]^-H^+$, $[Ir(CH_3)I_3(CO_2)]^-H^+$, $Ir_4(CO)_{12}$, $IrCl_3.3H_2O$, $IrBr_3.3H_2O$, iridium metal, $Ir_2O_3$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$. Chloride-free complexes of iridium such as acetates, oxalates and acetoacetates are usually employed as starting materials. The iridium catalyst concentration in the liquid reaction composition may be in the range of 100 to 6000 ppm. The carbonylation of methanol utilizing iridium catalyst is well known and is generally described in U.S. Pat. Nos. 5,942,460; 5,932,764; 5,883,295; 5,877,348; 5,877,347; and 5,696,284, which are hereby incorporated by reference.

A halogen co-catalyst/promoter is generally used in combination with the Group VIII metal catalyst component. Methyl iodide is a preferred halogen promoter. Preferably, the concentration of halogen promoter in the reaction medium ranges from 1 wt. % to 50 wt. %, and preferably from 2 wt. % to 30 wt. %.

The halogen promoter may be combined with the salt stabilizer/co-promoter compound. Particularly preferred are iodide or acetate salts, e.g., lithium iodide or lithium acetate.

Other promoters and co-promoters may be used as part of the catalytic system of the present invention as described in U.S. Pat. No. 5,877,348, which is hereby incorporated by reference. Suitable promoters are selected from ruthenium, osmium, tungsten, rhenium, zinc, cadmium, indium, gallium, mercury, nickel, platinum, vanadium, titanium, copper, aluminum, tin, antimony, and are more preferably selected from ruthenium and osmium. Specific co-promoters are described in U.S. Pat. No. 6,627,770, which is incorporated herein by reference.

A promoter may be present in an effective amount up to the limit of its solubility in the liquid reaction composition and/or any liquid process streams recycled to the carbonylation reactor from the acetic acid recovery stage. When used, the promoter is suitably present in the liquid reaction composition at a molar ratio of promoter to metal catalyst of 0.5:1 to 15:1, preferably 2:1 to 10:1, more preferably 2:1 to 7.5:1. A suitable promoter concentration is 400 to 5000 ppm.

In one embodiment, the temperature of the carbonylation reaction in the reactor is preferably from 150° C. to 250° C., e.g., from 150° C. to 225° C., or from 150° C. to 200° C. The pressure of the carbonylation reaction is preferably from 1 to 20 MPa, preferably 1 to 10 MPa, most preferably 1.5 to 5 MPa. Acetic acid is typically manufactured in a liquid phase reaction at a temperature from about 150° C. to about 200° C. and a total pressure of from about 2 to about 5 MPa.

In one embodiment, reaction mixture comprises a reaction solvent or mixture of solvents. The solvent is preferably compatible with the catalyst system and may include pure alcohols, mixtures of an alcohol feedstock, and/or the desired carboxylic acid and/or esters of these two compounds. In one embodiment, the solvent and liquid reaction medium for the (low water) carbonylation process is preferably acetic acid.

Water may be formed in situ in the reaction medium, for example, by the esterification reaction between methanol reactant and acetic acid product. In some embodiments, water is introduced to reactor together with or separately from other components of the reaction medium. Water may be separated from the other components of reaction product withdrawn from reactor and may be recycled in controlled amounts to maintain the required concentration of water in the reaction medium. Preferably, the concentration of water maintained in the reaction medium ranges from 0.1 wt. % to 16 wt. %, e.g., from 1 wt. % to 14 wt. %, or from 1 wt. % to 3 wt. % of the total weight of the reaction product.

The desired reaction rates are obtained even at low water concentrations by maintaining in the reaction medium an ester of the desired carboxylic acid and an alcohol, desirably the alcohol used in the carbonylation, and an additional iodide ion that is over and above the iodide ion that is present as hydrogen iodide. An example of a preferred ester is methyl acetate. The additional iodide ion is desirably an iodide salt, with lithium iodide (LiI) being preferred. It has been found, as described in U.S. Pat. No. 5,001,259, that under low water concentrations, methyl acetate and lithium iodide act as rate promoters only when relatively high concentrations of each of these components are present and that the promotion is higher when both of these components are present simultaneously. The absolute concentration of iodide ion content is not a limitation on the usefulness of the present invention.

In low water carbonylation, the additional iodide over and above the organic iodide promoter may be present in the catalyst solution in amounts ranging from 2 wt. % to 20 wt. %, e.g., from 2 wt. % to 15 wt. %, or from 3 wt. % to 10 wt. %; the methyl acetate may be present in amounts ranging from 0.5 wt. % to 30 wt. %, e.g., from 1 wt. % to 25 wt. %, or from 2 wt. % to 20 wt. %; and the lithium iodide may be present in amounts ranging from 5 wt. % to 20 wt. %, e.g., from 5 wt. % to 15 wt. %, or from 5 wt. % to 10 wt. %. The catalyst may be present in the catalyst solution in amounts ranging from 200 wppm to 2000 wppm, e.g., from 200 wppm to 1500 wppm, or from 500 wppm to 1500 wppm.

Hydrogenation Reaction

The carbonylation system may be integrated with an acetic acid hydrogenation process to produce ethanol with the following hydrogenation reaction conditions and catalysts.

The acetic acid, along with water, may be vaporized at the reaction temperature, following which the vaporized acetic acid can be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

Some embodiments of the process of hydrogenating acetic acid to form ethanol according to one embodiment of the invention may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, or from 100 kPa to 1500 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Contact or residence time can also vary widely, depending upon such variables as amount of acetic acid, catalyst, reactor, temperature and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

The hydrogenation of acetic acid to form ethanol is preferably conducted in the presence of a hydrogenation catalyst. Suitable hydrogenation catalysts include catalysts comprising a first metal and optionally one or more of a second metal, a third metal or any number of additional metals, optionally on a catalyst support. The first and optional second and third metals may be selected from Group IB, IIB, IIIB, IVB, VB, VIB, VIIB, VIII transition metals, a lanthanide metal, an actinide metal or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, and ruthenium/iron. Exemplary catalysts are further described in U.S. Pat. No. 7,608,744 and U.S. Pub. No. 2010/0029995, the entireties of which are incorporated herein by reference. In another embodiment, the catalyst comprises a Co/Mo/S catalyst of the type described in U.S. Pub. No. 2009/0069609, the entirety of which is incorporated herein by reference.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. In embodiments of the invention where the first metal comprises platinum, it is preferred that the catalyst comprises platinum in an amount less than 5 wt. %, e.g., less than 3 wt. % or less than 1 wt. %, due to the high commercial demand for platinum.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. Most preferably, the second metal is selected from tin and rhenium.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 5 wt. %. For catalysts comprising two or more metals, the two or more metals may be alloyed with one another, or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from both the first and second metals. In preferred embodiments, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal is preferably from 0.05 to 4 wt. %, e.g., from 0.1 to 3 wt. %, or from 0.1 to 2 wt. %.

In addition to one or more metals, in some embodiments of the present invention, the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 97 wt. %, or from 80 to 95 wt. %. In preferred embodiments that utilize a modified support, the support modifier is present in an amount from 0.1 to 50 wt. %, e.g., from 0.2 to 25 wt. %, from 0.5 to 15 wt. %, or from 1 to 8 wt. %, based on the total weight of the catalyst. The metals of the catalysts may be dispersed throughout the support, layered throughout the support, coated on the outer surface of the support (i.e., egg shell), or decorated on the surface of the support.

As will be appreciated by those of ordinary skill in the art, support materials are selected such that the catalyst system is suitably active, selective and robust under the process conditions employed for the formation of ethanol.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

The catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $Co_2O_3$, and $Bi_2O_3$.

In another embodiment, the support modifier may be a basic modifier that has a low volatility or no volatility. Such basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. The basic support modifier may be selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). If the basic support modifier comprises calcium metasilicate, it is preferred that at least a portion of the calcium metasilicate is in crystalline form.

A preferred silica support material is SS61138 High Surface Area (HSA) Silica Catalyst Carrier from Saint Gobain N or Pro. The Saint-Gobain N or Pro SS61138 silica exhibits the following properties: contains approximately 95 wt. % high surface area silica; surface area of about 250 $m^2/g$; median pore diameter of about 12 nm; average pore volume of about 1.0 $cm^3/g$ as measured by mercury intrusion porosimetry; and packing density of about 0.352 $g/cm^3$ (22 $lb/ft^3$).

Another preferred silica support material is KA-160 silica spheres from Süd-Chemie having a nominal diameter of about 5 mm, a density of about 0.562 g/ml, an absorptivity of about 0.583 g H$_2$O/g support, a surface area of about 160 to 175 m$^2$/g, and a pore volume of about 0.68 ml/g.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197485 referred to above, the entireties of which are incorporated herein by reference.

In particular, the hydrogenation of acetic acid may achieve favorable conversion of acetic acid and favorable selectivity and productivity to ethanol. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments, a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 1 ton of ethanol per hour, e.g., at least 15 tons of ethanol per hour or at least 30 tons of ethanol per hour. In terms of ranges, for large scale industrial production of ethanol, the process of the present invention may produce from 0.1 to 160 tons of ethanol per hour, e.g., from 15 to 160 tons of ethanol per hour or from 30 to 80 tons of ethanol per hour. Ethanol production from fermentation, due the economies of scale, typically does not permit the single facility ethanol production that may be achievable by employing embodiments of the present invention.

In various embodiments of the present invention, the crude ethanol product produced by the hydrogenation process, before any subsequent processing, such as purification and separation, will typically comprise acetic acid, ethanol and water. Exemplary compositional ranges for the crude ethanol product are provided in Table 1. The "others" identified in Table 1 may include, for example, esters, ethers, aldehydes, ketones, alkanes, and carbon dioxide.

TABLE 1

CRUDE ETHANOL PRODUCT

| Component | Conc. (wt. %) | Conc. (wt. %) | Conc. (wt. %) | Conc. (wt. %) |
|---|---|---|---|---|
| Ethanol | 5 to 70 | 30 to 70 | 45 to 70 | 25 to 50 |
| Acetic Acid | 0 to 90 | 1 to 80 | 2 to 70 | 5 to 70 |
| Water | 5 to 60 | 15 to 60 | 20 to 60 | 20 to 40 |
| Ethyl Acetate | 0 to 35 | 0 to 15 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product comprises acetic acid in an amount less than 20 wt. %, e.g., less than 15 wt. %, less than 10 wt. % or less than 5 wt. %. In terms of ranges, the acetic acid concentration of Table 1 may range from 0.1 wt. % to 20 wt. %, e.g., 0.2 wt. % to 15 wt. %, from 0.5 wt. % to 10 wt. % or from 1 wt. % to 5 wt. %. In embodiments having lower amounts of acetic acid, the conversion of acetic acid is preferably greater than 75%, e.g., greater than 85% or greater than 90%. In addition, the selectivity to ethanol may also be preferably high, and is preferably greater than 75%, e.g., greater than 85% or greater than 90%.

Integration Carbonylation and Hydrogenation

Figure 3:
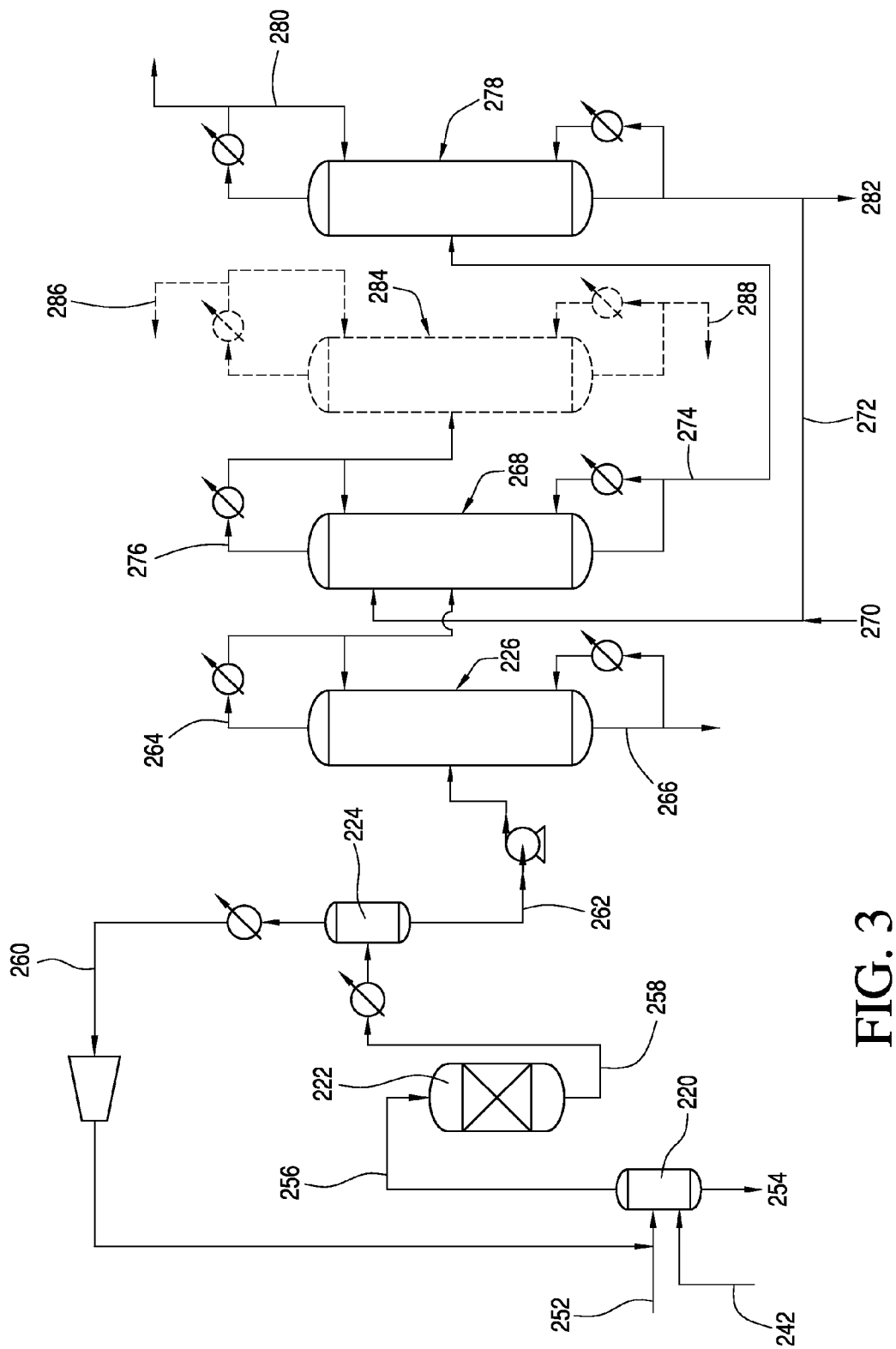
FIG. 3 is a schematic diagram of an ethanol separation process having four columns in accordance with an embodiment of the present invention.
Figure 4:
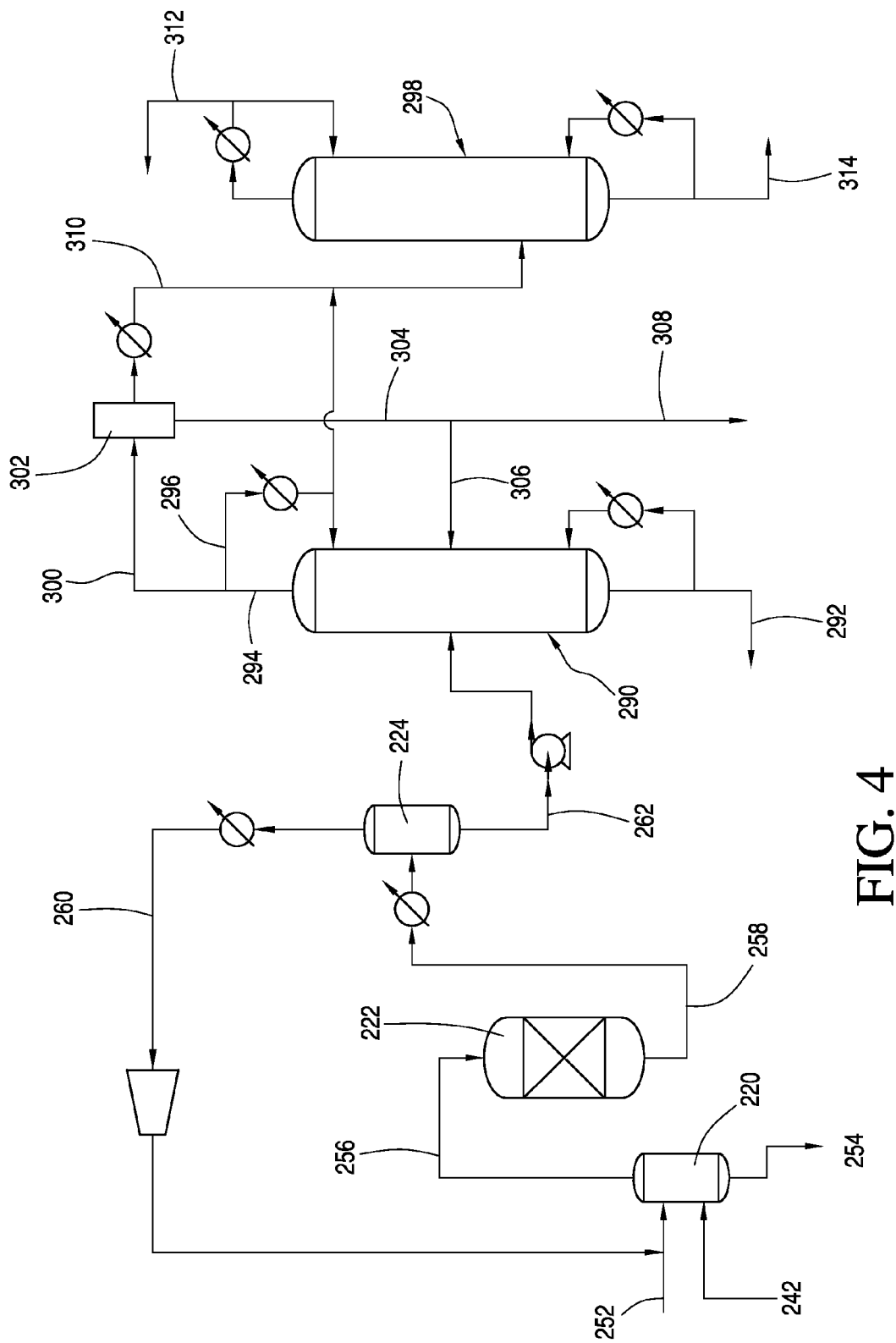
FIG. 4 is a schematic diagram of another ethanol separation process having two columns with an intervening water separation in accordance with an embodiment of the present invention.
Figure 5:
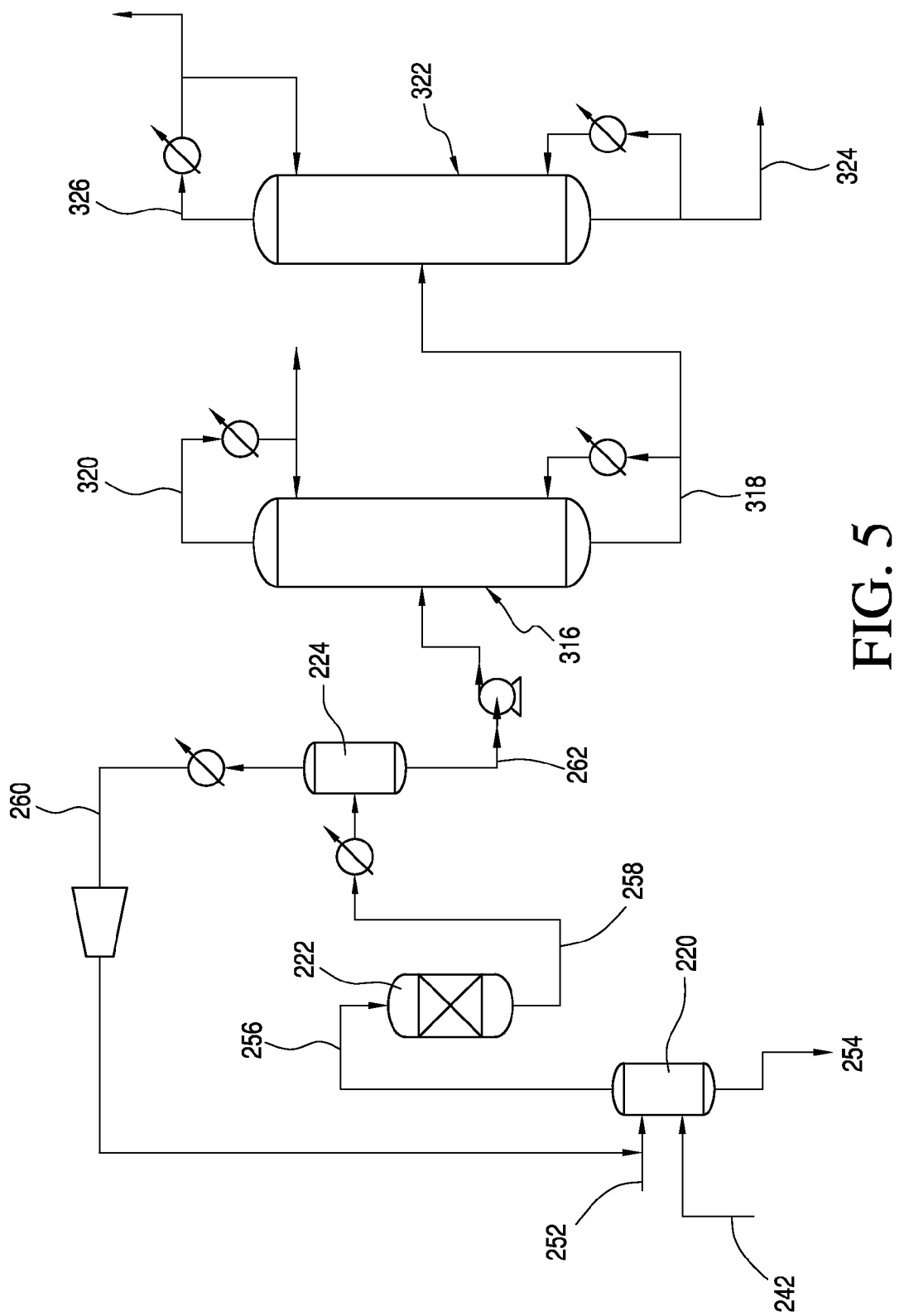
FIG. 5 is a schematic diagram of another hydrogenation process having two columns in accordance with an embodiment of the present invention.

FIG. 2 shows an exemplary integrated carbonylation and hydrogenation process 200, which comprises carbonylation system 202, hydrogenation zone 204, and hydrogenation separation zone 206. Carbonylation system 202 carbonylation reactor 210, flasher 214, rectification tower 216, and phase separator, e.g., decanter, 218. Hydrogenation reaction zone 204 comprises vaporizer 220 and hydrogenation reactor 222. Hydrogenation separation zone 206 comprises flasher 224 and column 226, also referred to as an "acid separation column." FIGS. 3-5 are exemplary hydrogenation processes that may be combined with the carbonylation system as described in FIG. 2.

In carbonylation system 202, methanol feed stream 228 comprises methanol and/or reactive derivatives thereof and carbon monoxide 230 are fed to a lower portion of carbonylation reactor 210. Suitable reactive derivatives of methanol include methyl acetate, dimethyl ether, methyl formate, and mixtures thereof may be included in methanol feed stream 228. At least some of the methanol and/or reactive derivative thereof will be converted to, and hence present as, methyl acetate in the liquid reaction composition by reaction with acetic acid product or solvent. The concentration in the liquid reaction composition of methyl acetate is suitably in the range of from 0.5 wt. % to 70 wt. %, e.g., from 0.5 wt. % to 50 wt. %, from 1 wt. % to 35 wt. %, or from 1 wt. % to 20 wt. %.

Reactor 210 is preferably either a stirred vessel, e.g., CSTR, or bubble-column type vessel, with or without an agitator, within which the reaction medium is maintained, preferably automatically, at a predetermined level. This predetermined level may remain substantially constant during normal operation. Into reactor 210, methanol, carbon monoxide, and sufficient water may be continuously introduced as needed to maintain at least a finite concentration of water in the reaction medium. In one embodiment, carbon monoxide, e.g., in the gaseous state, is continuously introduced into reactor 210, desirably below agitator, which is used to stir the contents. The temperature of reactor 210 may be controlled, as indicated above. Carbon monoxide feed 230 is introduced at a rate sufficient to maintain the desired total reactor pressure.

The gaseous carbon monoxide feed is preferably thoroughly dispersed through the reaction medium by agitator. A gaseous purge is desirably vented via an off-gas line (not shown) from reactor 210 to prevent buildup of gaseous by-products, such as methane, carbon dioxide, and hydrogen, and to maintain a carbon monoxide partial pressure at a given total reactor pressure.

The crude acetic acid product is drawn off from the reactor 210 at a rate sufficient to maintain a constant level therein. Crude acetic acid product in 234 is directed to flasher 214.

In flasher 214, the crude acetic acid product is separated to obtain a volatile ("vapor") stream 236 comprising acetic acid, methyl acetate, halogen promoter, i.e., methyl iodide, and water, and a less volatile stream 238 comprising a catalyst-containing solution. The catalyst-containing solution in line 238 comprises acetic acid containing the rhodium and the iodide salt along with lesser quantities of methyl acetate, methyl iodide, and water. The less volatile stream 238 preferably is recycled to reactor 210. Vapor stream 236 also comprises methyl iodide, methyl acetate, water, and permanganate reducing compounds ("PRC's").

Vapor stream 236 from flasher 214 is directed to rectification tower 216. In column 216, vapor stream 236 from the flasher is separated into an overhead stream 240 and an acetic acid stream 242. Overhead stream 240 comprises water, methyl iodide, and/or methyl acetate. Overhead stream 240 may also comprise acetic acid. Hence, the acetic acid, which may also comprise water, is continuously withdrawn via line 242 and conveyed to hydrogenation reaction zone 204. As stated above, acetic acid may comprises from 0.15 wt. % to 25 wt. % water. Thus, the present invention provides for producing acetic acid that is suitable for hydrogenation.

Optionally, sidestream in line 232 may be withdrawn from column 216. Sidestream in line 232 comprises acetic acid, which may also comprise water, may be withdrawn and directly fed to vaporizer 220 in the hydrogenation zone. In another embodiment, residue stream 242 may comprise acetic acid and heavy components and may be returned to reactor 210. The optional sidestream in line 232 may contain acetic acid with fewer impurities than residue stream in line 242.

As shown in FIG. 2, overhead stream 240 is preferably condensed and directed to an overhead phase separation unit, as shown by overhead receiver decanter 218. In a preferred embodiment, overhead stream 240 comprises more than 95% of the halogen promoter from vapor stream 236. In a preferred embodiment, overhead stream 240 comprises more than 95% of methyl acetate from vapor stream 236. In a preferred embodiment, overhead stream 240 comprises more than 95% water from vapor stream 236. Conditions are desirably maintained in the process such that overhead stream 240, once in decanter 218, will separate into a light phase and a heavy phase. Generally, overhead stream 240 is cooled to a temperature sufficient to condense and separate the condensable methyl iodide, methyl acetate, acetaldehyde and other carbonyl components, and water into two phases, condensed light phase 246 and condensed heavy liquid phase 248. A gaseous portion of stream 240 may include carbon monoxide, and other noncondensable gases such as methyl iodide, carbon dioxide, hydrogen, and the like and is vented from the decanter 218 via stream 244.

Condensed light phase 246 from decanter 218 preferably comprises water, acetic acid, and permanganate reducing compounds ("PRC's"), as well as quantities of methyl iodide and methyl acetate. The condensed light phase 246, in some embodiments, may be returned, either directly or indirectly, to rectification tower 216 or to flasher 214. In a preferred embodiment, a portion of condensed light phase 246 may be recycles to flasher 214 as a washing liquid to facilitate with removing catalyst and halogen promoter in the liquid recycle stream 238. For example, a portion of condensed light phase 246a may be recycled to rectification tower 216.

Condensed heavy liquid phase 248 from decanter 218 will generally comprise methyl iodide, methyl acetate, and PRC's. Condensed heavy liquid phase 248, in some embodiments, may be recirculated, either directly or indirectly, to reactor 210 or flasher 214. In a preferred embodiment, a portion of condensed heavy liquid phase 248a may be recycles to flasher 214 as a washing liquid to facilitate with removing catalyst and halogen promoter in the liquid recycle stream 238. In addition, a portion of condensed heavy liquid phase 248 can be recycled to reactor 210, with a slip stream (not shown), generally a small amount, e.g., from 5 to 40 vol. %, or from 5 to 20 vol. %, of the heavy liquid phase being directed to a PRC removal system. This slip stream of heavy liquid phase 248 may be treated individually or may be combined with condensed light liquid phase 246 for further distillation and extraction of carbonyl impurities in accordance with one embodiment of the present invention.

In one embodiment, a water stream in line 250 may be fed to flasher 214 to facilitate with the removal of catalyst or halogen promoters in liquid recycle stream 238. In addition, in a preferred embodiment, water from a downstream reaction or purification process may be used as a source for water stream in line 250. For example, in the downstream hydrogenation of acetic acid process, water is separated as a residue during a purification process in line 266 and it may be fed to rectification tower 216 to facilitate with the removal of catalyst or halogen promoters. Water in stream 266 may be combined with water from other sources, such as condensed heavy phase 248a, condensed light phase 246a, or outside source 250 before feeding to rectification tower 216.

In an embodiment of the present invention, a stream of acetic acid is recovered from the carbonylation process that is substantially free of any entrained materials from the carbonylation reaction by feeding water streams from other portions of the purification process to flasher 214. In an embodiment, the present invention provides for production efficiencies by recycling at least one water stream from the hydrogenation of acetic acid process to the flasher of the carbonylation of methanol, which beneficially reduces or eliminates the contamination of methyl iodide or entrained material in the acetic acid product in line 242. For example, as a result of the washing using at least recycled streams 246a, 248a, and 266, residue 242 from distillation column is substantially free of catalyst or halogen promoters. Furthermore, the distillation column removes some of the water from vapor stream 236 and residue 242. Therefore, residue in line 242 comprises acetic acid and water and, preferably, is conveyed, e.g., directly, to hydrogenation reaction zone 204.

The purified acetic acid stream, in some embodiments, comprises methyl acetate, e.g., in an amount ranging from 0.01 wt. % to 10 wt. % or from 0.1 wt. % to 5 wt. %. This methyl acetate, in preferred embodiments, may be reduced to form methanol and/or ethanol. In addition to acetic acid, water, and methyl acetate, the purified acetic acid stream may comprise halogens, e.g., methyl iodide, which may be removed from the purified acetic acid stream. In some embodiments, there may be a guard bed to further remove iodides, including methyl iodide, from the acetic acid in line 244 prior to being directed to hydrogenation system 204.

In hydrogenation reaction zone 204, hydrogen feed line 252 and stream 242 comprising acetic acid is fed to vaporizer 220. Vapor feed stream 256 is withdrawn and fed to hydrogenation reactor 222. In one embodiment, lines 252 and 242 may be combined and jointly fed to the vaporizer 220. The temperature of vapor feed stream 220 is preferably from 100° C. to 350° C., e.g., from 120° C. to 310° C. or from 150° C. to 300° C. Vapor feed stream 256 comprises from 0.15 wt. % to 25 wt. % water. Any feed that is not vaporized is removed from vaporizer 220 via stream 254, as shown in FIG. 2, and may be recycled thereto or discarded. In addition, although FIG. 2 shows line 256 being directed to the top of reactor 222, line 256 may be directed to the side, upper portion, or bottom of reactor 222. Further modifications and additional components to reaction zone 204 are described below.

Reactor 222 contains the catalyst that is used in the hydrogenation of the carboxylic acid, preferably acetic acid. During the hydrogenation process, a crude ethanol product is withdrawn, preferably continuously, from reactor 222 via line 258 and directed to separation zone 206.

Separation zone 206 comprises flasher 224, and first column 226. Further columns may be included as need to further separate and purify the crude ethanol product as shown in FIG. 3. The crude ethanol product may be condensed and fed to flasher 224, which, in turn, provides a vapor stream and a liquid stream. Flasher 224 may operate at a temperature of from 20° C. to 250° C., e.g., from 30° C. to 250° C. or from 60° C. to 200° C. The pressure of flasher 224 may be from 50 kPa to 2000 kPa, e.g., from 75 kPa to 1500 kPa or from 100 kPa to 1000 kPa.

The vapor stream exiting flasher 224 may comprise hydrogen and hydrocarbons, which may be purged and/or returned to reaction zone 204 via line 260. As shown in FIG. 2, the returned portion of the vapor stream passes through a compressor and is combined with the hydrogen feed and co-fed to vaporizer 220.

The liquid from flasher 224 is withdrawn and pumped as a feed composition via line 262 to the side of column 226, which may be referred to as the first column when multiple columns are used as shown in FIG. 3. Column 226 may also be referred to as an "acid separation column." The contents of line 262 typically will be substantially similar to the product obtained directly from the reactor 222, and may, in fact, also be characterized as a crude ethanol product. However, the feed composition in line 262 preferably has substantially no hydrogen, carbon dioxide, methane or ethane, which are removed by flasher 224. Exemplary compositions of line 262 are provided in Table 2. It should be understood that liquid line 262 may contain other components, not listed, such as additional components in the feed.

TABLE 2

| FEED COMPOSITION | | | |
|---|---|---|---|
| | Conc. (wt. %) | Conc. (wt. %) | Conc. (wt. %) |
| Ethanol | 5 to 70 | 30 to 70 | 25 to 50 |
| Acetic Acid | <90 | 1 to 80 | 2 to 70 |
| Water | 5 to 60 | 15 to 60 | 20 to 60 |
| Ethyl Acetate | <20 | 0.001 to 15 | 1 to 12 |
| Acetaldehyde | <10 | 0.001 to 3 | 0.1 to 3 |
| Acetal | <5 | 0.001 to 2 | 0.005 to 1 |
| Acetone | <5 | 0.0005 to 0.05 | 0.001 to 0.03 |
| Other Alcohols | <8 | <0.1 | <0.05 |
| Other Esters | <5 | <0.005 | <0.001 |
| Other Ethers | <5 | <0.005 | <0.001 |

The amounts indicated as less than (<) in the tables throughout the present application are preferably not present and if present may be present in trace amounts or in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. The "other alcohols" in Table 3 may include, but are not limited to, methanol, isopropanol, n-propanol, n-butanol or mixtures thereof. In one embodiment, the feed composition, e.g., line 262, may comprise propanol, e.g., isopropanol and/or n-propanol, in an amount from 0.001 to 0.1 wt. %, from 0.001 to 0.05 wt. % or from 0.001 to 0.03 wt. %. It should be understood that these other components may be carried through in any of the distillate or residue streams described herein.

Optionally, the crude ethanol product may pass through one or more membranes to separate hydrogen and/or other non-condensable gases. In other optional embodiments, the crude ethanol product may be fed directly to the acid separation column as a vapor feed and the non-condensable gases may be recovered from the overhead of the column.

When the content of acetic acid in line 262 is less than 5 wt. %, acid separation column 226 may be skipped and line 262 may be introduced directly to a second column, e.g., a "light ends column." In addition, column 226 may be operated to initially remove a substantial portion of water as the residue.

In the embodiment shown in FIG. 2, line 262 is introduced in the lower part of first column 226, e.g., lower half or lower third. Depending on the acetic acid conversion and operation of column 226, unreacted acetic acid, water, and other heavy components, if present, are removed from the composition in line 266 and are withdrawn, preferably continuously, as residue. In preferred embodiments, the presence of larger amounts of water in line 262 allows separation of a majority of water in line 266 along with substantially all the acetic acid in residue stream 266.

As discussed above, all or a portion of residue stream 266 may be recycled to carbonylation system 202. Residue stream 266 comprises water and acetic acid and may be used to reduce the amount of catalyst or halogen promoters in acetic acid stream 242. In an embodiment, residue stream 266 is fed to flasher 214 from at least a relatively higher position than crude acetic acid stream 234.

In another embodiment, all or a portion of residue stream 266 may be recycled to reaction zone 204 to produce additional ethanol. In addition, residue stream 266 may be separated into a water stream and an acetic acid stream, and either stream may be returned to reaction zone 204. In other embodiments, residue stream 266 may be a dilute acid stream that may be treated in a weak acid recovery system or sent to a reactive distillation column to convert the acid to esters.

First column 226 also forms an overhead distillate, which is withdrawn via stream 264, and which may be further processed to recover ethanol.

Ethanol Recovery

Ethanol may be recovered from the liquid stream 262 using several different separation processes. FIGS. 3-5 illustrate exemplary ethanol separation processes. For purposes of convenience, carbonylation system 202 is not shown in FIGS. 3-5 with each of these exemplary processes, but it is understood that the exemplary ethanol separations processes may be combined with the carbonylation system 202.

In one embodiment, the contents of liquid stream 262 are substantially similar to the reaction mixture obtained from the reaction zone, except that the composition has been depleted of hydrogen, carbon dioxide, methane and/or ethane, which are removed by separator 224. Liquid stream 262 may also be referred to as a crude ethanol product. Exemplary components of liquid stream 262 are provided in Table 2 above. Optionally, the crude ethanol product in line 258 or liquid stream 262 may be further fed to an esterification reactor, hydrogenolysis reactor, or combination thereof. An esterification reactor may be used to consume residual acetic acid present in the crude ethanol product to further reduce the amount of acetic acid that would otherwise need to be removed. Hydrogenolysis may be used to convert ethyl acetate in the crude ethanol product to ethanol.

In the embodiment shown in FIG. 3, liquid stream 262 is introduced in the lower part of first column 226, e.g., lower half or lower third. In first column 226, also referred to as an acid separation column, removes acetic acid, a portion of the water, and other heavy components, if present, from the feed, preferably continuously, as residue, 266. In one embodiment, a portion of the residue may be returned and/or recycled back to hydrogenation reaction zone 204 via line 266. Recycling the acetic acid in line 266 to the vaporizer 224 may reduce the amount of heavies that need to be purged from vaporizer 224. Reducing the amount of heavies to be purged may improve efficiencies of the process while reducing byproducts.

First column 226 also forms an overhead distillate, which is withdrawn in line 264, and which may be condensed and refluxed, for example, at a ratio from 10:1 to 1:10, e.g., from 3:1 to 1:3 or from 1:2 to 2:1.

When column 226 is operated under standard atmospheric pressure, the temperature of the residue exiting in line 266 preferably is from 95° C. to 120° C., e.g., from 110° C. to 117° C. or from 111° C. to 115° C. The temperature of the distillate exiting in line 264 preferably is from 70° C. to 110° C., e.g., from 75° C. to 95° C. or from 80° C. to 90° C. Column 226 preferably operates at ambient pressure. In other embodiments, the pressure of first column 226 may range from 0.1 kPa to 510 kPa, e.g., from 1 kPa to 475 kPa or from 1 kPa to 375 kPa. Exemplary components of the distillate and residue compositions for first column 226 are provided in Table 3 below. It should also be understood that the distillate and residue may also contain other components, not listed, such as components in the feed. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

ACID COLUMN 226 (FIG. 3)

| | Conc. (wt. %) | Conc. (wt. %) | Conc. (wt. %) |
|---|---|---|---|
| Distillate | | | |
| Ethanol | 20 to 75 | 30 to 70 | 40 to 65 |
| Water | 10 to 40 | 15 to 35 | 20 to 35 |
| Acetic Acid | <2 | 0.001 to 0.5 | 0.01 to 0.2 |
| Ethyl Acetate | <60 | 5.0 to 40 | 10 to 30 |
| Acetaldehyde | <10 | 0.001 to 5 | 0.01 to 4 |
| Acetal | <0.1 | <0.1 | <0.05 |
| Acetone | <0.05 | 0.001 to 0.03 | 0.01 to 0.025 |
| Residue | | | |
| Acetic Acid | 60 to 100 | 70 to 95 | 85 to 92 |
| Water | <30 | 1 to 20 | 1 to 15 |
| Ethanol | <1 | <0.9 | <0.07 |

As shown in Table 3, without being bound by theory, it has surprisingly and unexpectedly been discovered that when any amount of acetal is detected in the feed that is introduced to the acid separation column 226, the acetal appears to decompose in the column such that less or even no detectable amounts are present in the distillate and/or residue.

The distillate in line 264 preferably comprises ethanol, ethyl acetate, and water, along with other impurities, which may be difficult to separate due to the formation of binary and tertiary azeotropes. To further separate distillate, line 264 is introduced to the second column 268, also referred to as the "light ends column," preferably in the middle part of column 268, e.g., middle half or middle third. Preferably the second column 268 is an extractive distillation column, and an extraction agent is added thereto via lines 270 and/or 272. Extractive distillation is a method of separating close boiling components, such as azeotropes, by distilling the feed in the presence of an extraction agent. The extraction agent preferably has a boiling point that is higher than the compounds being separated in the feed. In preferred embodiments, the extraction agent is comprised primarily of water. As indicated above, the first distillate in line 264 that is fed to the second column 268 comprises ethyl acetate, ethanol, and water. These compounds tend to form binary and ternary azeotropes, which decrease separation efficiency. As shown, in one embodiment the extraction agent comprises the third residue in line 272. Preferably, the recycled third residue in line 272 is fed to second column 268 at a point higher than the first distillate in line 264. In one embodiment, the recycled third residue in line 272 is fed near the top of second column 268 or fed, for example, above the feed in line 264 and below the reflux line from the condensed overheads. In a tray column, the third residue in line 272 is continuously added near the top of the second column 268 so that an appreciable amount of the third residue is present in the liquid phase on all of the trays below. In another embodiment, the extraction agent is fed from a source outside of the process via line 270 to second column 268. Preferably this extraction agent comprises water.

The molar ratio of the water in the extraction agent to the ethanol in the feed to the second column is preferably at least 0.5:1, e.g., at least 1:1 or at least 3:1. In terms of ranges, preferred molar ratios may range from 0.5:1 to 8:1, e.g., from 1:1 to 7:1 or from 2:1 to 6.5:1. Higher molar ratios may be used but with diminishing returns in terms of the additional ethyl acetate in the second distillate and decreased ethanol concentrations in the second column distillate.

In one embodiment, an additional extraction agent, such as water from an external source, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N'-dimethyl-1,3-propanediamine, N,N'-dimethylethylenediamine, diethylene triamine, hexamethylene diamine and 1,3-diaminopentane, an alkylated thiopene, dodecane, tridecane, tetradecane and chlorinated paraffins, may be added to second column 268. Some suitable extraction agents include those described in U.S. Pat. Nos. 4,379,028, 4,569,726, 5,993,610 and 6,375,807, the entire contents and disclosure of which are hereby incorporated by reference. The additional extraction agent may be combined with the recycled third residue in line 272 and co-fed to the second column 268. The additional extraction agent may also be added separately to the second column 268. In one aspect, the extraction agent comprises an extraction agent, e.g., water, derived from an external source via line 270 and none of the extraction agent is derived from the third residue.

Second column 268 may be a tray or packed column. In one embodiment, second column 268 is a tray column having from 5 to 70 trays, e.g., from 15 to 50 trays or from 20 to 45 trays. Although the temperature and pressure of second column 268 may vary, when at atmospheric pressure the temperature of the second residue exiting in line 274 preferably is from 60° C. to 90° C., e.g., from 70° C. to 90° C. or from 80° C. to 90° C. The temperature of the second distillate exiting in line 276 from second column 268 preferably is from 50° C. to 90° C., e.g., from 60° C. to 80° C. or from 60° C. to 70° C. Column 268 may operate at atmospheric pressure. In other embodiments, the pressure of second column 268 may range from 0.1 kPa to 510 kPa, e.g., from 1 kPa to 475 kPa or from 1 kPa to 375 kPa. Exemplary components for the distillate and residue compositions for second column 268 are provided in Table 4 below. It should be understood that the distillate and residue may also contain other components, not listed, such as components in the feed.

TABLE 4

SECOND COLUMN 268 (FIG. 3)

| | Conc. (wt. %) | Conc. (wt. %) | Conc. (wt. %) |
|---|---|---|---|
| Distillate | | | |
| Ethyl Acetate | 10 to 99 | 25 to 95 | 50 to 93 |
| Acetaldehyde | <25 | 0.5 to 15 | 1 to 8 |
| Water | <25 | 0.5 to 20 | 4 to 16 |
| Ethanol | <30 | 0.001 to 15 | 0.01 to 5 |
| Acetal | <5 | 0.001 to 2 | 0.01 to 1 |
| Residue | | | |
| Water | 30 to 90 | 40 to 85 | 50 to 85 |
| Ethanol | 10 to 75 | 15 to 60 | 20 to 50 |
| Ethyl Acetate | <3 | 0.001 to 2 | 0.001 to 0.5 |
| Acetic Acid | <0.5 | 0.001 to 0.3 | 0.001 to 0.2 |

In preferred embodiments, the recycling of the third residue promotes the separation of ethyl acetate from the residue of the second column 268. For example, the weight ratio of ethyl acetate in the second residue to second distillate preferably is less than 0.4:1, e.g., less than 0.2:1 or less than 0.1:1. In embodiments that use an extractive distillation column with water as an extraction agent as the second column 268, the weight ratio of ethyl acetate in the second residue to ethyl acetate in the second distillate approaches zero.

The weight ratio of ethanol in the second residue to second distillate preferably is at least 3:1, e.g., at least 6:1, at least 8:1, at least 10:1 or at least 15:1. All or a portion of the third residue is recycled to the second column. In one embodiment, all of the third residue may be recycled until process reaches a steady state and then a portion of the third residue is recycled with the remaining portion being purged from the system. The composition of the second residue will tend to have lower amounts of ethanol than when the third residue is not recycled. As the third residue is recycled, the composition of the second residue, as provided in Table 4, comprises less than 30 wt. % of ethanol, e.g., less than 20 wt. % or less than 15 wt. %. The majority of the second residue preferably comprises water. Notwithstanding this effect, the extractive distillation step advantageously also reduces the amount of ethyl acetate that is sent to the third column, which is highly beneficial in ultimately forming a highly pure ethanol product.

As shown, the second residue from second column 268, which comprises ethanol and water, is fed via line 274 to third column 278, also referred to as the "product column." More preferably, the second residue in line 274 is introduced in the lower part of third column 278, e.g., lower half or lower third. Third column 278 recovers ethanol, which preferably is substantially pure with respect to organic impurities and other than the azeotropic water content, as the distillate in line 280. The distillate of third column 278 preferably is refluxed as shown in FIG. 3, for example, at a reflux ratio from 1:10 to 10:1, e.g., from 1:3 to 3:1 or from 1:2 to 2:1. The third residue in line 272, which comprises primarily water, preferably is returned to the second column 268 as an extraction agent as described above. In one embodiment, a first portion of the third residue in line 272 is recycled to the second column and a second portion is purged and removed from the system via line 282. In one embodiment, once the process reaches steady state, the second portion of water to be purged is substantially similar to the amount water formed in the hydrogenation of acetic acid. In one embodiment, a portion of the third residue may be used to hydrolyze any other stream, such as one or more streams comprising ethyl acetate.

Although FIG. 3 shows third residue being directly recycled to second column 268, third residue may also be returned indirectly, for example, by storing a portion or all of the third residue in a tank (not shown) or treating the third residue to further separate any minor components such as aldehydes, higher molecular weight alcohols, or esters in one or more additional columns (not shown).

Third column 278 is preferably a tray column as described above and operates at atmospheric pressure or optionally at pressures above or below atmospheric pressure. The temperature of the third distillate exiting in line 280 preferably is from 60° C. to 110° C., e.g., from 70° C. to 100° C. or from 75° C. to 95° C. The temperature of the third residue in line 272 preferably is from 70° C. to 115° C., e.g., from 80° C. to 110° C. or from 85° C. to 105° C. Exemplary components of the distillate and residue compositions for third column 278 are provided in Table 5 below. It should be understood that the distillate and residue may also contain other components, not listed, such as components in the feed.

TABLE 5

THIRD COLUMN 278 (FIG. 3)

| | Conc. (wt. %) | Conc. (wt. %) | Conc. (wt. %) |
|---|---|---|---|
| Distillate | | | |
| Ethanol | 75 to 96 | 80 to 96 | 85 to 96 |
| Water | <12 | 1 to 9 | 3 to 8 |
| Acetic Acid | <12 | 0.0001 to 0.1 | 0.005 to 0.05 |

TABLE 5-continued

THIRD COLUMN 278 (FIG. 3)

|  | Conc. (wt. %) | Conc. (wt. %) | Conc. (wt. %) |
|---|---|---|---|
| Ethyl Acetate | <12 | 0.0001 to 0.05 | 0.005 to 0.025 |
| Acetaldehyde | <12 | 0.0001 to 0.1 | 0.005 to 0.05 |
| Diethyl Acetal | <12 | 0.0001 to 0.05 | 0.005 to 0.025 |
| Residue |  |  |  |
| Water | 75 to 100 | 80 to 100 | 90 to 100 |
| Ethanol | <0.8 | 0.001 to 0.5 | 0.005 to 0.05 |
| Ethyl Acetate | <1 | 0.001 to 0.5 | 0.005 to 0.2 |
| Acetic Acid | <2 | 0.001 to 0.5 | 0.005 to 0.2 |

In one embodiment, the third residue in line 272 is withdrawn from third column 278 at a temperature higher than the operating temperature of the second column 268. Preferably, the third residue in line 272 is integrated to heat one or more other streams or is reboiled prior to be returned to the second column 268.

Any of the compounds that are carried through the distillation process from the feed or crude reaction product generally remain in the third distillate in amounts of less 0.1 wt. %, based on the total weight of the third distillate composition, e.g., less than 0.05 wt. % or less than 0.02 wt. %. In one embodiment, one or more sidestreams may remove impurities from any of the columns in the system. Preferably at least one sidestream is used to remove impurities from the third column 278. The impurities may be purged and/or retained within the system.

The third distillate in line 280 may be further purified to form an anhydrous ethanol product stream, i.e., "finished anhydrous ethanol," using one or more additional separation systems, such as, for example, distillation columns, adsorption units, membranes, or molecular sieves. Suitable adsorption units include pressure swing adsorption units and thermal swing adsorption unit.

Returning to second column 268, the second distillate preferably is refluxed as shown in FIG. 3, optionally at a reflux ratio of 1:10 to 10:1, e.g., from 1:5 to 5:1 or from 1:3 to 3:1. The second distillate in line 276 may be purged or recycled to the reaction zone. In an optional embodiment, the second distillate in line 276 may be further processed in an optional fourth column 284, also referred to as the "acetaldehyde removal column." Whether optional fourth column 284 is required depends primarily on the acetaldehyde concentration in line 276. In fourth column 284 the second distillate is separated into a fourth distillate, which comprises acetaldehyde, in line 286 and a fourth residue, which comprises ethyl acetate, in line 288. The fourth distillate preferably is refluxed at a reflux ratio from 1:20 to 20:1, e.g., from 1:15 to 15:1 or from 1:10 to 10:1, and a portion of the fourth distillate is returned to the reaction zone 204. For example, the fourth distillate may be combined with the acetic acid feed, added to the vaporizer 220, or added directly to the reactor 222. The fourth distillate preferably is co-fed with the acetic acid in feed line 242 to vaporizer 220. Without being bound by theory, since acetaldehyde may be hydrogenated to form ethanol, the recycling of a stream that contains acetaldehyde to the reaction zone increases the yield of ethanol and decreases byproduct and waste generation. In another embodiment, the acetaldehyde may be collected and utilized, with or without further purification, to make useful products including but not limited to n-butanol, 1,3-butanediol, and/or crotonaldehyde and derivatives.

The fourth residue of fourth column 284 may be purged via line 288. The fourth residue primarily comprises ethyl acetate and ethanol, which may be suitable for use as a solvent mixture or in the production of esters. In one preferred embodiment, the acetaldehyde is removed from the second distillate in fourth column 284 such that no detectable amount of acetaldehyde is present in the residue of column 284.

Fourth column 284 is preferably a tray column as described above and preferably operates above atmospheric pressure. In one embodiment, the pressure is from 120 kPa to 5,000 kPa, e.g., from 200 kPa to 4,500 kPa, or from 400 kPa to 3,000 kPa. In a preferred embodiment fourth column 284 may operate at a pressure that is higher than the pressure of the other columns.

The temperature of the fourth distillate exiting in line 286 preferably is from 60° C. to 110° C., e.g., from 70° C. to 100° C. or from 75° C. to 95° C. The temperature of the residue in line 290 preferably is from 70° C. to 115° C., e.g., from 80° C. to 110° C. or from 85° C. to 110° C. Exemplary components of the distillate and residue compositions for fourth column 284 are provided in Table 6 below. It should be understood that the distillate and residue may also contain other components, not listed, such as components in the feed.

TABLE 6

OPTIONAL FOURTH COLUMN 284 (FIG. 3)

|  | Conc. (wt. %) | Conc. (wt. %) | Conc. (wt. %) |
|---|---|---|---|
| Distillate |  |  |  |
| Acetaldehyde | 2 to 80 | 2 to 50 | 5 to 40 |
| Ethyl Acetate | <90 | 30 to 80 | 40 to 75 |
| Ethanol | <30 | 0.001 to 25 | 0.01 to 20 |
| Water | <25 | 0.001 to 20 | 0.01 to 15 |
| Residue |  |  |  |
| Ethyl Acetate | 40 to 100 | 50 to 100 | 60 to 100 |
| Ethanol | <40 | 0.001 to 30 | 0.01 to 15 |
| Water | <25 | 0.001 to 20 | 2 to 15 |
| Acetaldehyde | <1 | 0.001 to 0.5 | Not detectable |
| Acetal | <3 | 0.001 to 2 | 0.01 to 1 |

In one embodiment, a portion of the third residue in line 272 is recycled to second column 268. In one embodiment, recycling the third residue further reduces the aldehyde components in the second residue and concentrates these aldehyde components in second distillate in line 276 and thereby sent to the fourth column 284, wherein the aldehydes may be more easily separated. The third distillate, e.g. intermediate stream, in line 280 may have lower concentrations of aldehydes and esters due to the recycling of third residue in line 272.

FIG. 4 illustrates another exemplary separation system used to produce ethanol from liquid stream 262. Liquid stream 262 is introduced in the middle or lower portion of a first column 290, also referred to as acid-water column. For purposes of convenience, the columns in each exemplary separation process, may be referred as the first, second, third, etc., columns, but it is understood that first column 290 in FIG. 4 operates differently than the first column 226 of FIG. 3. In one embodiment, no entrainers are added to first column 290. In FIG. 4, first column 290, water and unreacted acetic acid, along with any other heavy components, if present, are removed from liquid stream 262 and are withdrawn, preferably continuously, as a first residue in line 292. Preferably, a substantial portion of the water in the crude ethanol product that is fed to first column 290 may be removed in the first residue, for example, up to about 90% of the water from the crude ethanol product, and more preferably up to about 75%. First column 290 also forms a first distillate, which is withdrawn in line 294.

When column 290 is operated under about 170 kPa, the temperature of the residue exiting in line 292 preferably is from 90° C. to 130° C., e.g., from 95° C. to 120° C. or from 100° C. to 115° C. The temperature of the distillate exiting in line 294 preferably is from 60° C. to 90° C., e.g., from 65° C. to 85° C. or from 70° C. to 80° C. In some embodiments, the pressure of first column 290 may range from 0.1 kPa to 510 kPa, e.g., from 1 kPa to 475 kPa or from 1 kPa to 375 kPa.

The first distillate in line 294 comprises water, in addition to ethanol and other organics. In terms of ranges, the concentration of water in the first distillate in line 294 preferably is from 4 wt. % to 38 wt. %, e.g., from 7 wt. % to 32 wt. %, or from 7 to 25 wt. %. A portion of first distillate in line 296 may be condensed and refluxed, for example, at a ratio from 10:1 to 1:10, e.g., from 3:1 to 1:3 or from 1:2 to 2:1. It is understood that reflux ratios may vary with the number of stages, feed locations, column efficiency and/or feed composition. Operating with a reflux ratio of greater than 3:1 may be less preferred because more energy may be required to operate the first column 290. The condensed portion of the first distillate may also be fed to a second column 298.

The remaining portion of the first distillate in 300 is fed to a water separation unit 302. Water separation unit 302 may be an adsorption unit, membrane, molecular sieves, extractive column distillation, or a combination thereof. A membrane or an array of membranes may also be employed to separate water from the distillate. The membrane or array of membranes may be selected from any suitable membrane that is capable of removing a permeate water stream from a stream that also comprises ethanol and ethyl acetate.

In a preferred embodiment, water separation unit 302 is a pressure swing adsorption (PSA) unit. The PSA unit is optionally operated at a temperature from 30° C. to 160° C., e.g., from 80° C. to 140° C., and a pressure from 0.01 kPa to 550 kPa, e.g., from 1 kPa to 150 kPa. The PSA unit may comprise two to five beds. Water separation unit 302 may remove at least 95% of the water from the portion of first distillate in line 300, and more preferably from 99% to 99.99% of the water from the first distillate, in a water stream 304. All or a portion of water stream 304 may be returned to column 290 in line 306, where the water preferably is ultimately recovered from column 290 in the first residue in line 292. Additionally or alternatively, all or a portion of water stream 304 may be purged via line 308. The remaining portion of first distillate exits the water separation unit 302 as ethanol mixture stream 310. Ethanol mixture stream 310 may have a low concentration of water of less than 10 wt. %, e.g., less than 6 wt. % or less than 2 wt. %. Exemplary components of ethanol mixture stream 310 and first residue in line 292 are provided in Table 7 below. It should also be understood that these streams may also contain other components, not listed, such as components derived from the feed.

TABLE 7

| FIRST COLUMN 290 WITH PSA (FIG. 4) | | | |
|---|---|---|---|
| | Conc. (wt. %) | Conc. (wt. %) | Conc. (wt. %) |
| Ethanol Mixture Stream | | | |
| Ethanol | 20 to 95 | 30 to 95 | 40 to 95 |
| Water | <10 | 0.01 to 6 | 0.1 to 2 |
| Acetic Acid | <2 | 0.001 to 0.5 | 0.01 to 0.2 |
| Ethyl Acetate | <60 | 1 to 55 | 5 to 55 |

TABLE 7-continued

| FIRST COLUMN 290 WITH PSA (FIG. 4) | | | |
|---|---|---|---|
| | Conc. (wt. %) | Conc. (wt. %) | Conc. (wt. %) |
| Acetaldehyde | <10 | 0.001 to 5 | 0.01 to 4 |
| Acetal | <0.1 | <0.1 | <0.05 |
| Acetone | <0.05 | 0.001 to 0.03 | 0.01 to 0.025 |
| Residue | | | |
| Acetic Acid | <90 | 1 to 50 | 2 to 35 |
| Water | 30 to 100 | 45 to 95 | 60 to 90 |
| Ethanol | <1 | <0.9 | <0.3 |

Preferably, ethanol mixture stream 310 is not returned or refluxed to first column 290. The condensed portion of the first distillate in line 296 may be combined with ethanol mixture stream 310 to control the water concentration fed to the second column 298. For example, in some embodiments the first distillate may be split into equal portions, while in other embodiments, all of the first distillate may be condensed or all of the first distillate may be processed in the water separation unit. In FIG. 4, the condensed portion in line 296 and ethanol mixture stream 310 are co-fed to second column 298. In other embodiments, the condensed portion in line 296 and ethanol mixture stream 310 may be separately fed to second column 298. The combined distillate and ethanol mixture has a total water concentration of greater than 0.5 wt. %, e.g., greater than 2 wt. % or greater than 5 wt. %. In terms of ranges, the total water concentration of the combined distillate and ethanol mixture may be from 0.5 to 15 wt. %, e.g., from 2 to 12 wt. %, or from 5 to 10 wt. %.

The second column 298 in FIG. 4, also referred to as the "light ends column," removes ethyl acetate and acetaldehyde from the first distillate in line 294 and/or ethanol mixture stream 310. Ethyl acetate and acetaldehyde are removed as a second distillate in line 312 and ethanol is removed as the second residue in line 314. Second column 298 may be a tray column or packed column. In one embodiment, second column 298 is a tray column having from 5 to 70 trays, e.g., from 15 to 50 trays or from 20 to 45 trays.

Second column 298 operates at a pressure ranging from 0.1 kPa to 510 kPa, e.g., from 10 kPa to 450 kPa or from 50 kPa to 350 kPa. Although the temperature of second column 298 may vary, when at about 20 kPa to 70 kPa, the temperature of the second residue exiting in line 314 preferably is from 30° C. to 75° C., e.g., from 35° C. to 70° C. or from 40° C. to 65° C. The temperature of the second distillate exiting in line 312 preferably is from 20° C. to 55° C., e.g., from 25° C. to 50° C. or from 30° C. to 45° C.

The total concentration of water fed to second column 298 preferably is less than 10 wt. %, as discussed above. When first distillate in line 296 and/or ethanol mixture stream 310 comprises minor amounts of water, e.g., less than 1 wt. % or less than 0.5 wt. %, additional water may be fed to the second column 298 as an extractive agent in the upper portion of the column. A sufficient amount of water is preferably added via the extractive agent such that the total concentration of water fed to second column 298 is from 1 to 10 wt. % water, e.g., from 2 to 6 wt. %, based on the total weight of all components fed to second column 298. If the extractive agent comprises water, the water may be obtained from an external source or from an internal return/recycle line from one or more of the other columns or water separators.

Suitable extractive agents may also include, for example, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N'-dimethyl-1,3-propanediamine, N,N'-dimethylethylenediamine, diethylene triamine, hexamethylene diamine and 1,3-diaminopentane, an alkylated thiopene, dodecane, tridecane, tetradecane, chlorinated paraffins, or a combination thereof. When extractive agents are used, a suitable recovery system, such as a further distillation column, may be used to recycle the extractive agent.

Exemplary components for the second distillate and second residue compositions for the second column 298 are provided in Table 8, below. It should be understood that the distillate and residue may also contain other components, not listed in Table 8.

TABLE 8

SECOND COLUMN 298 (FIG. 4)

|  | Conc. (wt. %) | Conc. (wt. %) | Conc. (wt. %) |
|---|---|---|---|
| Second Distillate |  |  |  |
| Ethyl Acetate | 5 to 90 | 10 to 80 | 15 to 75 |
| Acetaldehyde | <60 | 1 to 40 | 1 to 35 |
| Ethanol | <45 | 0.001 to 40 | 0.01 to 35 |
| Water | <20 | 0.01 to 10 | 0.1 to 5 |
| Second Residue |  |  |  |
| Ethanol | 80 to 99.5 | 85 to 99.5 | 90 to 99.5 |
| Water | <20 | 0.001 to 15 | 0.01 to 10 |
| Ethyl Acetate | <1 | 0.001 to 2 | 0.001 to 0.5 |
| Acetic Acid | <0.5 | <0.01 | 0.001 to 0.01 |

The second distillate in line 312, which comprises ethyl acetate and/or acetaldehyde, preferably is refluxed as shown in FIG. 4, for example, at a reflux ratio from 1:30 to 30:1, e.g., from 1:10 to 10:1 or from 1:3 to 3:1. In one aspect, not shown, the second distillate 312 or a portion thereof may be returned to reaction zone 204. The ethyl acetate and/or acetaldehyde in the second distillate may be further reacted in reaction zone 204.

In optional embodiment, the second distillate in line 312 and/or a refined second distillate, or a portion of either or both streams, may be further separated to produce an acetaldehyde-containing stream and an ethyl acetate-containing stream similar to optional fourth column in FIG. 4. This may allow a portion of either the resulting acetaldehyde-containing stream or ethyl acetate-containing stream to be recycled to reactor 222 while purging the other stream. The purge stream may be valuable as a source of either ethyl acetate and/or acetaldehyde.

FIG. 5 illustrates another exemplary separation system used to produce ethanol from liquids stream 262. Liquid stream 262 is introduced in the upper part of first column 316, e.g., upper half or upper third. In one embodiment, no entrainers are added to first column 316. In first column 316, a weight majority of the ethanol, water, acetic acid, and other heavy components, if present, are removed from liquid stream 262 and are withdrawn, preferably continuously, as residue in line 318. First column 316 also forms an overhead distillate, which is withdrawn in line 320, and which may be condensed and refluxed, for example, at a ratio from 30:1 to 1:30, e.g., from 10:1 to 1:10 or from 1:5 to 5:1. The overhead distillate in stream 320 preferably comprises a weight majority of the ethyl acetate from liquid stream 262.

When column 316 is operated under about 170 kPa, the temperature of the residue exiting in line 318 preferably is from 70° C. to 155° C., e.g., from 90° C. to 130° C. or from 100° C. to 110° C. The base of column 316 may be maintained at a relatively low temperature by withdrawing a residue stream comprising ethanol, water, and acetic acid, thereby providing an energy efficiency advantage. The temperature of the distillate exiting in line 320 preferably at 170 kPa is from 75° C. to 100° C., e.g., from 75° C. to 83° C. or from 81° C. to 84° C. In some embodiments, the pressure of first column 316 may range from 0.1 kPa to 510 kPa, e.g., from 1 kPa to 475 kPa or from 1 kPa to 375 kPa. Exemplary components of the distillate and residue compositions for first column 316 are provided in Table 9 below. It should also be understood that the distillate and residue may also contain other components, not listed in Table 9.

TABLE 9

FIRST COLUMN 316 (FIG. 5)

|  | Conc. (wt. %) | Conc. (wt. %) | Conc. (wt. %) |
|---|---|---|---|
| Distillate |  |  |  |
| Ethyl Acetate | 10 to 85 | 15 to 80 | 20 to 75 |
| Acetaldehyde | 0.1 to 70 | 0.2 to 65 | 0.5 to 65 |
| Acetal | <0.1 | <0.1 | <0.05 |
| Acetone | <0.05 | 0.001 to 0.03 | 0.01 to 0.025 |
| Ethanol | 3 to 55 | 4 to 50 | 5 to 45 |
| Water | 0.1 to 20 | 1 to 15 | 2 to 10 |
| Acetic Acid | <2 | <0.1 | <0.05 |
| Residue |  |  |  |
| Acetic Acid | 0.01 to 35 | 0.1 to 30 | 0.2 to 25 |
| Water | 5 to 40 | 10 to 35 | 15 to 30 |
| Ethanol | 10 to 75 | 15 to 70 | 20 to 65 |

In an embodiment of the present invention, column 316 may be operated at a temperature where most of the water, ethanol, and acetic acid are removed from the residue stream and only a small amount of ethanol and water is collected in the distillate stream due to the formation of binary and tertiary azeotropes. The weight ratio of water in the residue in line 318 to water in the distillate in line 320 may be greater than 1:1, e.g., greater than 2:1. The weight ratio of ethanol in the residue to ethanol in the distillate may be greater than 1:1, e.g., greater than 2:1

The amount of acetic acid in the first residue may vary depending primarily on the conversion in reaction zone 204. In one embodiment, when the conversion is high, e.g., greater than 90%, the amount of acetic acid in the first residue may be less than 10 wt. %, e.g., less than 5 wt. % or less than 2 wt. %. In other embodiments, when the conversion is lower, e.g., less than 90%, the amount of acetic acid in the first residue may be greater than 10 wt. %.

The distillate preferably is substantially free of acetic acid, e.g., comprising less than 1000 wppm, less than 500 wppm or less than 100 wppm acetic acid. The distillate may be purged from the system or recycled in whole or part to reaction zone 204. In some embodiments, the distillate may be further separated, e.g., in a distillation column (not shown), into an acetaldehyde stream and an ethyl acetate stream. Either of these streams may be returned to the first reaction zone 204 or separated from system as a separate product.

Some species, such as acetals, may decompose in first column 316 such that very low amounts, or even no detectable amounts, of acetals remain in the distillate or residue.

To recover ethanol, the residue in line 318 may be further separated in a second column 322, also referred to as an "acid separation column." An acid separation column may be used when the acetic acid concentration in the first residue is greater than 1 wt. %, e.g., greater than 5 wt. %. The first residue in line 318 is introduced to second column 322 preferably in the top part of column 322, e.g., top half or top third. Second column 322 yields a second residue in line 324 comprising acetic acid and water, and a second distillate in line 326 comprising ethanol. Second column 322 may be a tray column or packed column. In one embodiment, second column 322 is a tray column having from 5 to 150 trays, e.g., from 15 to 50 trays or from 20 to 45 trays. Although the temperature and pressure of second column 322 may vary, when at atmospheric pressure the temperature of the second residue exiting in line 324 preferably is from 95° C. to 130° C., e.g., from 100° C. to 125° C. or from 110° C. to 120° C. The temperature of the second distillate exiting in line 326 preferably is from 60° C. to 105° C., e.g., from 75° C. to 100° C. or from 80° C. to 100° C. The pressure of second column 322 may range from 0.1 kPa to 510 kPa, e.g., from 1 kPa to 475 kPa or from 1 kPa to 375 kPa. Exemplary components for the distillate and residue compositions for second column 322 are provided in Table 10 below. It should be understood that the distillate and residue may also contain other components, not listed in Table 10.

TABLE 10

SECOND COLUMN 322 (FIG. 5)

|  | Conc. (wt. %) | Conc. (wt. %) | Conc. (wt. %) |
| --- | --- | --- | --- |
| Second Distillate |  |  |  |
| Ethanol | 70 to 99.9 | 75 to 98 | 80 to 95 |
| Ethyl Acetate | <10 | 0.001 to 5 | 0.01 to 3 |
| Acetaldehyde | <5 | 0.001 to 1 | 0.005 to 0.5 |
| Water | 0.1 to 30 | 1 to 25 | 5 to 20 |
| Second Residue |  |  |  |
| Acetic Acid | 0.1 to 45 | 0.2 to 40 | 0.5 to 35 |
| Water | 45 to 100 | 55 to 99.8 | 65 to 99.5 |
| Ethyl Acetate | <2 | <1 | <0.5 |
| Ethanol | <5 | 0.001 to 5 | <2 |

The weight ratio of ethanol in the second distillate in line 326 to ethanol in the second residue in line 324 preferably is at least 35:1. In one embodiment, the weight ratio of water in the second residue 324 to water in the second distillate 326 is greater than 2:1, e.g., greater than 4:1 or greater than 6:1. In addition, the weight ratio of acetic acid in the second residue 324 to acetic acid in the second distillate 326 preferably is greater than 10:1, e.g., greater than 15:1 or greater than 20:1. Preferably, the second distillate in line 326 is substantially free of acetic acid and may only contain, if any, trace amounts of acetic acid. Preferably, the second distillate in line 326 contains substantially no ethyl acetate.

The remaining water from the second distillate in line 326 may be removed in further embodiments of the present invention. Depending on the water concentration, the ethanol product may be derived from the second distillate in line 326. Some applications, such as industrial ethanol applications, may tolerate water in the ethanol product, while other applications, such as fuel applications, may require an anhydrous ethanol. The amount of water in the distillate of line 326 may be closer to the azeotropic amount of water, e.g., at least 4 wt. %, preferably less than 20 wt. %, e.g., less than 12 wt. % or less than 7.5 wt. %. Water may be removed from the second distillate in line 326 using several different separation techniques as described herein. Particularly preferred techniques include the use of distillation column, membranes, adsorption units, and combinations thereof.

Some of the residues withdrawn from the separation systems shown in FIGS. 3, 4, and 5, may comprise acetic acid and water. As discussed above, these residues may be returned and recycled to flasher 214 to facilitate with the removal of catalyst and/or halogen promoter in the residue 238. Thus, acetic acid side stream 242 may be recovered with substantially no or little catalyst and/or halogen promoter. Furthermore, the cost of using a recycled stream from within the integration system is substantially lower than using external resources.

In addition, depending on the amount of water and acetic acid contained in the residue of first column or residue of second column, the residue may be treated in one or more of the following processes. The following are exemplary processes for further treating the residue and it should be understood that any of the following may be used regardless of acetic acid concentration. When the residue comprises a majority of acetic acid, e.g., greater than 70 wt. %, the residue may be recycled to the reactor without any separation of the water. In one embodiment, the residue may be separated into an acetic acid stream and a water stream when the residue comprises a majority of acetic acid, e.g., greater than 50 wt. %. Acetic acid may also be recovered in some embodiments from the residue having a lower acetic acid concentration. The residue may be separated into the acetic acid and water streams by a distillation column or one or more membranes. If a membrane or an array of membranes is employed to separate the acetic acid from the water, the membrane or array of membranes may be selected from any suitable acid resistant membrane that is capable of removing a permeate water stream. The resulting acetic acid stream optionally is returned to the reaction zone 204. The resulting water stream may be used as an extractive agent or to hydrolyze an ester-containing stream in a hydrolysis unit.

In other embodiments, for example, where the residue comprises less than 50 wt. % acetic acid, possible options include one or more of: (i) returning a portion of the residue to reactor 108, (ii) neutralizing the acetic acid, (iii) reacting the acetic acid with an alcohol, or (iv) disposing of the residue in a waste water treatment facility. It also may be possible to separate a residue comprising less than 50 wt. % acetic acid using a weak acid recovery distillation column to which a solvent (optionally acting as an azeotroping agent) may be added. Exemplary solvents that may be suitable for this purpose include ethyl acetate, propyl acetate, isopropyl acetate, butyl acetate, vinyl acetate, diisopropyl ether, carbon disulfide, tetrahydrofuran, isopropanol, ethanol, and $C_3$-$C_{12}$ alkanes. When neutralizing the acetic acid, it is preferred that the residue comprises less than 10 wt. % acetic acid. Acetic acid may be neutralized with any suitable alkali or alkaline earth metal base, such as sodium hydroxide or potassium hydroxide. When reacting acetic acid with an alcohol, it is preferred that the residue comprises less than 50 wt. % acetic acid. The alcohol may be any suitable alcohol, such as methanol, ethanol, propanol, butanol, or mixtures thereof. The reaction forms an ester that may be integrated with other systems, such as carbonylation production or an ester production process. Preferably, the alcohol comprises ethanol and the resulting ester comprises ethyl acetate. Optionally, the resulting ester may be fed to the hydrogenation reactor.

In some embodiments, when the residue comprises very minor amounts of acetic acid, e.g., less than 5 wt. %, the residue may be disposed of to a waste water treatment facility without further processing. The organic content, e.g., acetic acid content, of the residue beneficially may be suitable to feed microorganisms used in a waste water treatment facility.

The columns shown in figures may comprise any distillation column capable of performing the desired separation and/or purification. Each column preferably comprises a tray column having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The associated condensers and liquid separation vessels that may be employed with each of the distillation columns may be of any conventional design and are simplified in the figures. Heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and one flasher are shown in the figures, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in the columns may vary. As a practical matter, pressures from 10 kPa to 3000 kPa will generally be employed in these zones although in some embodiments subatmospheric pressures or superatmospheric pressures may be employed. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

The final ethanol product produced by the processes of the present invention may be taken from a stream that primarily comprises ethanol from FIGS. 3, 4, and 5. The ethanol product may be an industrial grade ethanol comprising from 75 to 96 wt. % ethanol, e.g., from 80 to 96 wt. % or from 85 to 96 wt. % ethanol, based on the total weight of the ethanol product. Exemplary finished ethanol compositional ranges are provided below in Table 11.

TABLE 11

FINISHED ETHANOL COMPOSITIONS

| Component | Conc. (wt. %) | Conc. (wt. %) | Conc. (wt. %) |
|---|---|---|---|
| Ethanol | 75 to 96 | 80 to 96 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm.

In some embodiments, when further water separation is used, the ethanol product may be withdrawn as a stream from the water separation unit as discussed above. In such embodiments, the ethanol concentration of the ethanol product may be greater than indicated in Table 11, and preferably is greater than 97 wt. % ethanol, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including fuels, solvents, chemical feedstock, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, ethyl benzene, aldehydes, butadiene, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing ethanol, comprising the steps of:
reacting carbon monoxide with at least one reactant in a reactor containing a reaction medium to produce a reaction product comprising acetic acid, wherein the reaction medium comprises water, acetic acid, methyl acetate, a halogen promoter, and a first catalyst;
separating the reaction product in a flasher into a liquid recycle stream and a vapor stream comprising acetic acid, the halogen promoter, methyl acetate and water;
distilling the vapor stream in a rectification tower and withdrawing an overhead stream comprising more than 90% of the water from the reaction product and an acetic acid feed stream at a point below where the vapor stream is introduced to the tower;
condensing the overhead stream and biphasically separating the overhead stream into an aqueous stream and an organic stream;
refluxing a portion of the aqueous stream to the rectification tower;
directing a portion of the aqueous stream to the flasher as a washing liquid to remove the first catalyst from a vapor phase;
hydrogenating acetic acid of the acetic acid feed stream in the presence of a second catalyst and under conditions effective to form a crude ethanol product; and
recovering ethanol from the crude ethanol product.

2. The process of claim 1, wherein the rectification tower removes more than 95% of water from the reaction product in the overhead stream.

3. The process of claim 1, wherein the acetic acid feed stream comprises less than 5% of water from the reaction product.

4. The process of claim 1, wherein the rectification tower removes more than 95% of the halogen promoter from the reaction product in the overhead stream.

5. The process of claim 1, wherein the acetic acid feed stream comprises less than 5% of the halogen promoter from the reaction product.

6. The process of claim 1, wherein the acetic acid feed stream contains less than 3% of the halogen promoter.

7. The process of claim 1, wherein the rectification tower removes more than 95% of methyl acetate from the reaction product in the overhead stream.

8. The process of claim 1, wherein the acetic acid feed stream comprises less than 5% of methyl acetate from the reaction product.

9. The process of claim 1, wherein the acetic acid feed stream is not subjected to further purification prior to hydrogenation.

10. The process of claim 1, wherein the overhead stream further comprises methyl iodide, and/or methyl acetate.

11. The process of claim 1, further comprises separating at least a portion of the crude ethanol product to yield a distillate comprising ethanol, water, and ethyl acetate, and a residue comprising acetic acid and water.

12. The process of claim 11, wherein the residue comprises less than 90 wt. % acetic acid and from 30 wt. % to 100 wt. % water.

13. The process of claim 11, wherein the washing liquid comprises a portion of the residue.

14. The process of claim 11, wherein the distillate contains less than 2% of acetic acid.

15. The process of claim 1, wherein the second catalyst comprises a combination of metals selected from the group consisting of platinum/tin, platinum/ruthenium, platinum/rhenium, palladium/ruthenium, palladium/rhenium, cobalt/palladium, cobalt/platinum, cobalt/chromium, cobalt/ruthenium, silver/palladium, copper/palladium, nickel/palladium, gold/palladium, ruthenium/rhenium, and ruthenium/iron.

16. A process for producing ethanol, comprising the steps of:
reacting carbon monoxide with at least one reactant in a reactor containing a reaction medium to produce a reaction product comprising acetic acid, wherein the reaction medium comprises water, acetic acid, methyl acetate, a halogen promoter, and a first catalyst;
separating the reaction product in a flasher into a liquid recycle stream and a vapor stream comprising acetic acid, the halogen promoter, methyl acetate and water;
adding a washing liquid to the flasher to remove catalyst from a vapor phase such that the vapor stream comprises substantially no catalyst;
distilling the vapor stream in a rectification tower and withdrawing an acetic acid feed stream at a point below where the vapor stream is introduced to the tower;
hydrogenating acetic acid of the acetic acid feed stream in the presence of a second catalyst and under conditions effective to form a crude ethanol product; and
separating at least a portion of the crude ethanol product to yield a distillate comprising ethanol, water, and ethyl acetate, and a residue comprising acetic acid and water, wherein the washing liquid comprises a portion of the residue.

17. A process for producing ethanol, comprising the steps of:
reacting carbon monoxide with at least one reactant in a reactor containing a reaction medium to produce a reaction product comprising acetic acid, wherein the reaction medium comprises water, acetic acid, methyl acetate, a halogen promoter, and a first catalyst;
separating the reaction product in a flasher into a liquid recycle stream and a vapor stream comprising acetic acid, the halogen promoter, methyl acetate and water;
adding a washing liquid to the flasher to remove catalyst from a vapor phase such that the vapor stream comprises substantially no catalyst;
distilling the vapor stream in a rectification tower to form an acetic acid feed stream and an overhead stream, wherein the washing liquid comprises a portion of the overhead stream;
hydrogenating acetic acid of the acetic acid feed stream in the presence of a second catalyst and under conditions effective to form a crude ethanol product; and
recovering ethanol from the crude ethanol product.

18. The process of claim 17, wherein the acetic acid contains less than 3% of the halogen promoter.

19. The process of claim 17, further comprising the steps of condensing the overhead stream and biphasically separating the overhead stream into an aqueous stream and an organic stream, wherein the aqueous stream is refluxed to the rectification tower.

20. The process of claim 19, wherein the washing liquid comprises a portion of the aqueous stream and the organic stream.

* * * * *